US011311260B2

(12) United States Patent
Sano et al.

(10) Patent No.: US 11,311,260 B2
(45) Date of Patent: Apr. 26, 2022

(54) X-RAY PHASE IMAGING APPARATUS

(71) Applicant: Shimadzu Corporation, Kyoto (JP)

(72) Inventors: Satoshi Sano, Kyoto (JP); Koichi Tanabe, Kyoto (JP); Yukihisa Wada, Kyoto (JP); Satoshi Tokuda, Kyoto (JP); Akira Horiba, Kyoto (JP); Naoki Morimoto, Kyoto (JP)

(73) Assignee: Shimadzu Corporation, Kyoto (KE)

( * ) Notice: Subject to any disclaimer, the term of this patent is extended or adjusted under 35 U.S.C. 154(b) by 9 days.

(21) Appl. No.: 16/834,883

(22) Filed: Mar. 30, 2020

(65) Prior Publication Data
US 2020/0337659 A1 Oct. 29, 2020

(30) Foreign Application Priority Data

Apr. 24, 2019 (JP) .............................. JP2019-082459

(51) Int. Cl.
A61B 6/00 (2006.01)
G01N 23/041 (2018.01)
A61B 6/04 (2006.01)
G21K 1/06 (2006.01)

(52) U.S. Cl.
CPC ............ A61B 6/484 (2013.01); A61B 6/0487 (2020.08); A61B 6/4035 (2013.01); A61B 6/4291 (2013.01); A61B 6/4435 (2013.01); G01N 23/041 (2018.02); G21K 1/06 (2013.01); G01N 2223/1016 (2013.01); G01N 2223/3303 (2013.01); G01N 2223/3307 (2013.01); G01N 2223/427 (2013.01); G21K 2207/005 (2013.01)

(58) Field of Classification Search
None
See application file for complete search history.

(56) References Cited

U.S. PATENT DOCUMENTS

| 5,812,629 A * | 9/1998 | Clauser ................. A61B 6/466 378/62 |
| 9,046,466 B2 * | 6/2015 | Ouchi ................. G01N 23/041 |
| 9,597,050 B2 * | 3/2017 | Roessl ..................... A61B 6/06 |
| 9,726,622 B2 * | 8/2017 | Momose ........... G01N 23/20075 |
| 2012/0002785 A1 * | 1/2012 | Kaneko ................. G21K 1/067 378/62 |
| 2013/0010926 A1 * | 1/2013 | Tada .................... A61B 6/4291 378/62 |
| 2013/0034209 A1 * | 2/2013 | Ouchi ................. G02B 5/1871 378/62 |

(Continued)

FOREIGN PATENT DOCUMENTS

JP 2017-044603 A 3/2017
WO WO-2012026223 A1 * 3/2012 ............. A61B 6/484

(Continued)

Primary Examiner — Thomas R Artman
(74) Attorney, Agent, or Firm — Muir Patent Law, PLLC

(57) ABSTRACT

In this X-ray phase imaging apparatus, at least one of a plurality of gratings is composed of a plurality of grating portions arranged along a third direction perpendicular to a first direction along which a subject or an imaging system is moved by a moving mechanism and a second direction along which an X-ray source, a detection unit, and a plurality of grating portions are arranged. The plurality of grating portions are arranged such that adjacent grating portions overlap each other when viewed in the first direction.

13 Claims, 24 Drawing Sheets

(56) References Cited

U.S. PATENT DOCUMENTS

| | | | | |
|---|---|---|---|---|
| 2015/0036795 A1* | 2/2015 | Roessl | .................. | A61B 6/484 |
| | | | | 378/36 |
| 2016/0252470 A1* | 9/2016 | Momose | ................. | G21K 1/06 |
| | | | | 378/36 |
| 2018/0356355 A1 | 12/2018 | Momose et al. | | |
| 2020/0337659 A1* | 10/2020 | Sano | .................... | G01N 23/041 |
| 2021/0137476 A1* | 5/2021 | Sano | ...................... | A61B 6/484 |

FOREIGN PATENT DOCUMENTS

| | | | | |
|---|---|---|---|---|
| WO | WO-2012081376 A1 * | 6/2012 | ............... | G21K 1/06 |
| WO | WO-2015033552 A1 * | 3/2015 | ........... | A61B 6/4291 |

\* cited by examiner

X-RAY PHASE IMAGING APPARATUS

CROSS-REFERENCE TO THE RELATED APPLICATIONS

The priority application number JP2019-082459, entitled "X-ray phase imaging apparatus", filed on Apr. 24, 2019, and invented by Satoshi Sano, Koichi Tanabe, Yukihisa Wada, Satoshi Tokuda, Akira Horiba, and Naoki Morimoto, upon which this patent application is based is hereby incorporated by reference.

BACKGROUND OF THE INVENTION

Field of the Invention

The present invention relates to an X-ray phase imaging apparatus, and more particularly to an X-ray phase imaging apparatus for performing imaging while relatively moving a subject and an imaging system.

Description of the Background Art

Conventionally, an X-ray phase imaging apparatus for performing imaging while relatively moving a subject and an imaging system is known. Such an X-ray phase imaging apparatus is disclosed, for example, in Japanese Unexamined Patent Application Publication No. 2017-44603.

The Japanese Unexamined Patent Application Publication No. 2017-44603 discloses a radiation image generation apparatus (X-ray phase imaging apparatus) equipped with an imaging system including an X-ray source, a plurality of gratings, and a detection unit, a transport unit, and an image generation unit. In the radiation image generation apparatus disclosed in Japanese Unexamined Patent Application Publication No. 2017-44603, the X-ray source, the plurality of gratings, and the detection unit are arranged in this order along the optical axis direction of X-rays. The detection unit detects the X-rays emitted by the X-ray source and transmitted through the plurality of gratings. The image generation unit generates a phase-contrast image including an absorption image, a phase differential image, and a dark field image based on a plurality of images captured while moving the subject by the transport unit (while relatively moving the subject and the imaging system) along a predetermined direction (the direction of the grating pitch of the grating or the direction along which the grating extends) in a plane perpendicular to the optical axis direction. Note that the absorption image denotes an image obtained by imaging the difference in the absorption degree of X-rays due to a subject. Also, note that the phase differential image denotes an image obtained by imaging the phase shift of X-rays. Also, note that the dark field image denotes a visibility image obtained by a change in visibility based on small-angle scattering of an object.

In the X-ray phase imaging apparatus disclosed in Japanese Unexamined Patent Application Publication No. 2017-44603, by performing imaging while relatively moving a subject and an imaging system, even in cases where the size of the subject is larger than the size of the grating in the direction along which the subject and the imaging system are moved relatively (in the movement direction during imaging, the entire subject can be imaged. Therefore, in the X-ray phase imaging apparatus disclosed in Japanese Unexamined Patent Application Publication No. 2017-44603, it becomes possible to reduce the size of the grating in the movement direction during imaging.

However, in the X-ray phase imaging apparatus disclosed in Japanese Unexamined Patent Application Publication No. 2017-44603, although the grating can be reduced in size in the movement direction during imaging, the grating needs to be increased in size in a direction perpendicular to the movement direction during imaging in a plane perpendicular to the optical axis direction so that the subject does not protrude from the grating when imaging a relatively large subject. Note that a grating used in a conventional X-ray phase imaging apparatus as disclosed in Japanese Unexamined Patent Application Publication No. 2017-44603 has a large aspect ratio (the height (depth) of the grating relative to the grating pitch), so it is difficult to accurately produce a single grating having a large area.

Therefore, although not disclosed in Japanese Unexamined Patent Application Publication No. 2017-44603, in a conventional X-ray phase imaging apparatus as disclosed in Japanese Unexamined Patent Application Publication No. 2017-44603, when imaging a relatively large subject, it is conceivable to increase the area of the grating by arranging a plurality of gratings side by side in a direction perpendicular to the movement direction during imaging. As described above, when a plurality of gratings is arranged side by side, it is conceivable that the plurality of gratings is bonded to each other, but since the plurality of gratings is manufactured as separate members from each other, an unintended gap may be generated between the plurality of gratings adjacent to each other due to a manufacturing error.

For example, in a configuration in which a subject and an imaging system are relatively moved in the grating pitch direction of the grating (in a direction perpendicular to a direction along which the grating extends), a gap is generated in which the gratings are discontinuous in a direction along which the plurality of gratings is adjacent to each other (a direction along which the grating extends). In this case, when performing imaging while relatively moving the subject and the imaging system, a portion where the subject hardly passes through the grating may simply occur.

In addition, in a configuration in which a subject and an imaging system are relatively moved in a direction in which the grating extends (in a direction perpendicular to the grating pitch direction), a gap may be sometimes generated as a portion (a portion that does not function as a grating) having at least one of a pitch different from the grating pitch and an angle different from the angle of the grating pitch in a direction in which a plurality of gratings is adjacent to each other (in a grating pitch direction). Also in this case, when performing imaging while relatively moving the subject and the imaging system, the subject passes through a gap as a portion which does not function as a grating, so that a portion in which the subject hardly passes through the grating substantially occurs.

In this manner, when a portion in which the subject hardly passes through the grating is generated, a portion where the subject cannot be imaged is generated. Therefore, as disclosed in the X-ray phase imaging apparatus of Japanese Unexamined Patent Application Publication No. 2017-44603, in a configuration in which imaging is performed while relatively moving a subject and an imaging system, when a plurality of gratings is arranged side by side in order to increase the area in a direction perpendicular to a direction along which the subject and the imaging system are relatively moved, there may be a problem that a portion where the subject cannot be imaged is generated because a portion in which the subject hardly passes through the grating is generated.

SUMMARY OF THE INVENTION

The present invention has been made to solve the above-mentioned problems, and an object of the present invention is to provide an X-ray phase imaging apparatus capable of enlarging an area in a direction perpendicular to a direction in which a subject and an imaging system are relatively moved while suppressing occurrence of a portion where the subject cannot be imaged due to occurrence of a portion in which the subject hardly passes through the grating in a configuration in which imaging is performed while relatively moving the subject and the imaging system.

In order to achieve the above object, an X-ray phase imaging apparatus according to one aspect of the present invention includes: an X-ray source; a detection unit configured to detect X-rays emitted from the X-ray source; a plurality of gratings arranged between the X-ray source and the detection unit to allow the X-rays emitted from the X-ray source to pass therethrough; a moving mechanism configured to move 1) a subject arranged between the X-ray source and the detection unit or 2) an imaging system composed of the X-ray source, the detection unit and the plurality of gratings, along a direction in which the plurality of gratings extend or along a direction in which the plurality of gratings are arranged in a grating pitch; and an image processing unit configured to generate a phase-contrast image based on a plurality of images acquired based on signals detected by the detection unit with the subject and the imaging system being relatively moved with respect to each other, wherein at least one of the plurality of gratings is composed of a plurality of grating portions arranged along a third direction perpendicular to a first direction in which the subject or the imaging system is moved by the moving mechanism and a second direction in which the X-ray source, the detection unit, and the plurality of gratings are arranged, and wherein the plurality of grating portions are arranged so that adjacent grating portions overlap when viewed in the first direction.

According to the present invention, as described above, at least one of the plurality of gratings is composed of a plurality of grating portions arranged along a third direction perpendicular to a first direction in which a subject or an imaging system is moved by a moving mechanism and a second direction in which an X-ray source, a detection unit, and a plurality of gratings is arranged, and the plurality of grating portions are arranged such that adjacent grating portions overlap each other when viewed in the first direction.

With this, in the grating composed of the plurality of grating portions, it is possible to suppress the occurrence of a portion in which the subject hardly passes through the grating in the third direction in which the plurality of grating portions are arranged side by side when performing imaging while relatively moving the subject and the imaging system in the first direction. As a result, in the configuration in which imaging is performed while relatively moving the subject and the imaging system, it is possible to increase an area in a direction perpendicular to a direction in which the subject and the imaging system are relatively moved while suppressing the occurrence of a portion in which the subject cannot be imaged due to the occurrence of a portion in which the subject hardly passes through the grating.

DESCRIPTION OF THE PREFERRED EMBODIMENTS

Embodiments embodying the present invention will be explained with reference to the attached drawings.

Embodiment 1

Configuration of X-ray Phase Imaging Apparatus

With reference to FIG. 1 to FIG. 8, a configuration of an X-ray phase imaging apparatus 100 according to a first embodiment will be described.

Figure 1:
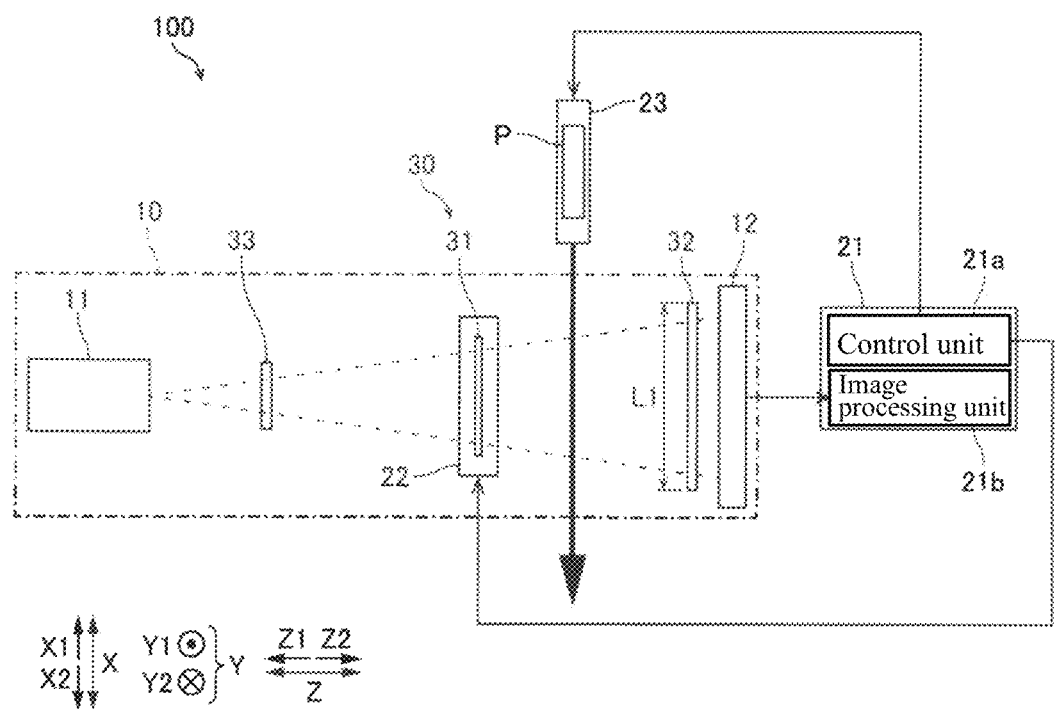
FIG. 1 is a diagram showing an entire configuration of an X-ray phase imaging apparatus according to a first embodiment.

As shown in FIG. 1, the X-ray phase imaging apparatus 100 is a device for imaging an interior of a subject P by utilizing a Talbot effect. The X-ray phase imaging apparatus 100 is provided with an imaging system 10, a processing unit 21, a grating position adjustment mechanism 22, and a subject moving mechanism 23. The imaging system 10 is composed of an X-ray tube 11, a detection unit 12, and a plurality of gratings 30. The plurality of gratings 30 includes a first grating 31, a second grating 32, and a third grating 33. Note that the X-ray tube 11 is an example of the "X-ray source" recited in claims. Also, note that the subject moving mechanism 23 is an example of the "moving mechanism" recited in claims.

In the X-ray phase imaging apparatus 100, the X-ray tube 11, the third grating 33, the first grating 31, the second grating 32, and the detection unit 12 are arranged in this order in the X-ray irradiation axis direction (in the optical axis direction, the Z-direction). That is, the first grating 31, the second grating 32, and the third grating 33 are arranged between the X-ray tube 11 and the detection unit 12. In this specification, note that the direction from the X-ray tube 11 toward the detection unit 12 is referred to as a Z2-direction, and the opposite direction is referred to as a Z1-direction. Also, note that the Z-direction is an example of the "second direction" recited in claims. In the first embodiment, the direction (A-direction) of the grating pitch D (see FIG. 2) of the plurality of gratings 30 and the direction (B-direction) in which the gratings 30 of the plurality of gratings 30 extend are referred to as an X-direction and a Y-direction, respectively. Also, in the first embodiment, note that the X-direction and the Y-direction are an example of the "first direction" and an example of the "third direction" recited in claims, respectively.

The X-ray tube 11 is an X-ray generator capable of generating X-rays by applying a high voltage. The X-ray tube 11 is configured to emit generated X-rays in the Z2-direction. The X-rays emitted from the X-ray tube 11 passes through the first grating 31, the second grating 32, and the third grating 33 arranged between the X-ray tube 11 and the detection unit 12.

The detection unit 12 detects the X-rays emitted from the X-ray tube 11 and converts the detected X-rays into electric signals. The detection unit 12 is, for example, an FPD (Flat Panel Detector). The detection unit 12 is composed of a plurality of conversion elements (not shown) and pixel electrodes (not shown) arranged on the plurality of conversion elements. The plurality of conversion elements and pixel electrodes are arranged side by side in the X-direction and Y-direction at predetermined pixel pitches. The detection signal (image signal) of the detection unit 12 is sent to an image processing unit 21b (described later) included in the processing unit 21.

Figure 2:
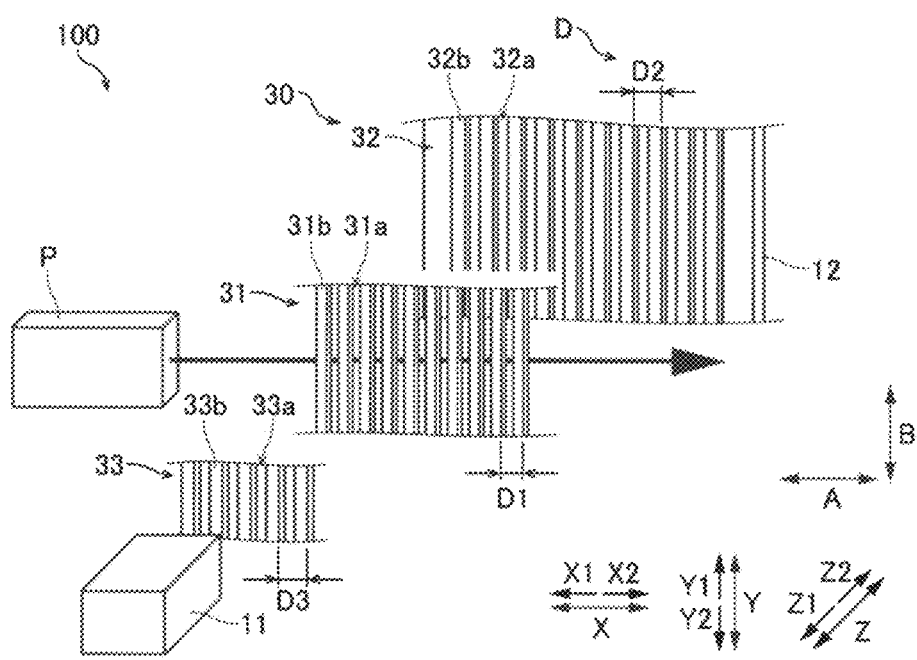
FIG. 2 is a diagram for explaining a configuration of a grating in the X-ray phase imaging apparatus according to the first embodiment.

As shown in FIG. 2, the first grating 31 has slits 31a and X-ray phase change portions 31b arranged in the X-direction (A-direction) at predetermined periods (grating pitches) D1. The slits 31a and the X-ray phase change portion 31b are each formed to extend in the Y-direction (B-direction). The first grating 31 is a so-called phase grating. As shown in FIG. 1, the first grating 31 is arranged between the X-ray tube 11 and the second grating G2 and is provided to form a self-image (by a Talbot effect) by the X-rays emitted from the X-ray tube 11. Note that a Talbot effect means that when coherent X-rays pass through the first grating 31 in which the slits 31a are formed, an image (self-image) of the first grating 31 is formed at a predetermined distance (Talbot distance) apart from the first grating 31.

As shown in FIG. 2, the second grating 32 has a plurality of X-ray transmission portions 32a and X-ray absorption portions 32b arranged in the X-direction (A-direction) at predetermined periods (grating pitches) D2. The X-ray transmission portion 32a and the X-ray absorption portion 32b are formed to extend in the Y-direction (B-direction). The second grating 32 is a so-called absorption grating. As shown in FIG. 1, the second grating 32 is arranged between the first grating 31 and the detection unit 12 and is configured to interfere with the self-image formed by the first grating 31. The second grating 32 is arranged at a position apart from the first grating 31 by a Talbot distance so as to make the self-image interfere with the second grating 32. As a result, in the X-ray phase imaging apparatus 100, the interference fringe (moiré fringe) 40 (see FIG. 8) generated by the interference of the self-image with the second grating 32 is detected as X-rays by the detection unit 12 arranged in the vicinity of of the second grating 32 on the downstream side (Z2 side).

As shown in FIG. 2, the third grating 33 has a plurality of slits 33a and X-ray absorption portions 33b arranged in the X-direction (A-direction) at predetermined intervals (pitches) D3. The slits 33a and the X-ray absorption portions 33b are each formed to extend in the Y-direction (B-direction). As shown in FIG. 1, the third grating 33 is arranged between the X-ray tube 11 and the first grating 31 and is irradiated with X-rays emitted from the X-ray tube 11. The third grating 33 is arranged so that the X-ray which has passed through each slit 33a is used as a linear light source corresponding to the position of each slit 33a. That is, the third grating 33 is provided to enhance the coherence of the X-rays emitted from the X-ray tube 11.

The processing unit 21 includes a control unit 21a and an image processing unit 21b.

The control unit 21a is configured to generate a moiré fringe 40 (see FIG. 8) on the detection surface of the detection unit 12 by controlling the grating position adjustment mechanism 22 to adjust the position of the first grating 31. The control unit 21a is configured to control the subject moving mechanism 23 to move the position of the subject moving mechanism 23 in the X-direction with respect to the imaging system 10. The control unit 21a includes, for example, a CPU (Central Processing Unit), a ROM (Read Only Memory), a RAM (Random Access Memory), and the like.

The image processing unit 21b is configured to generate an image such as a phase-contrast image 51 (see FIG. 4) based on a detection signal sent from the detection unit 12. The image processing unit 21b includes, for example, a processor such as a GPU (Graphics Processing Unit) and an FPGA (Field-Programmable Gate Array) configured for image-processing.

Figure 4:
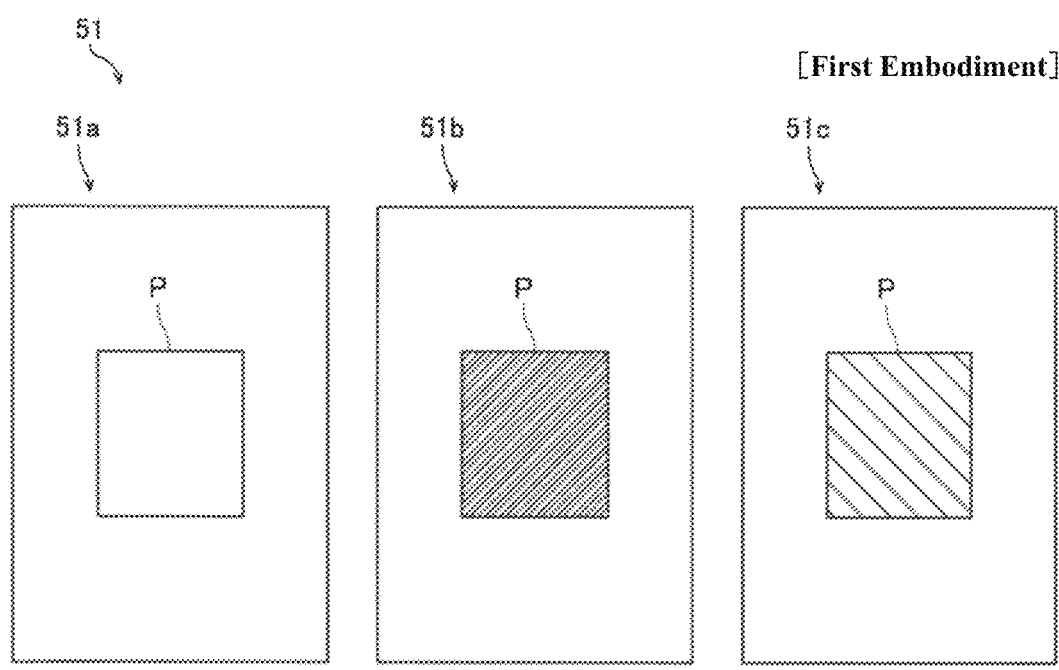
FIG. 4 is a diagram for explaining a phase-contrast image generated by an image processing unit of the X-ray phase imaging apparatus according to the first embodiment.

As shown in FIG. 4, the phase-contrast image 51 includes an absorption image 51a, a phase differential image 51b, and a dark field image 51c. The absorption image 51a is an image based on a difference in the absorption degree of X-rays. The phase differential image 51b is an image based on a phase shift of X-rays. The dark field image 51c is an image based on a change in visibility due to a small angle scattering of an object. The dark field image 51c is also called a small angle scattering image.

Figure 3:
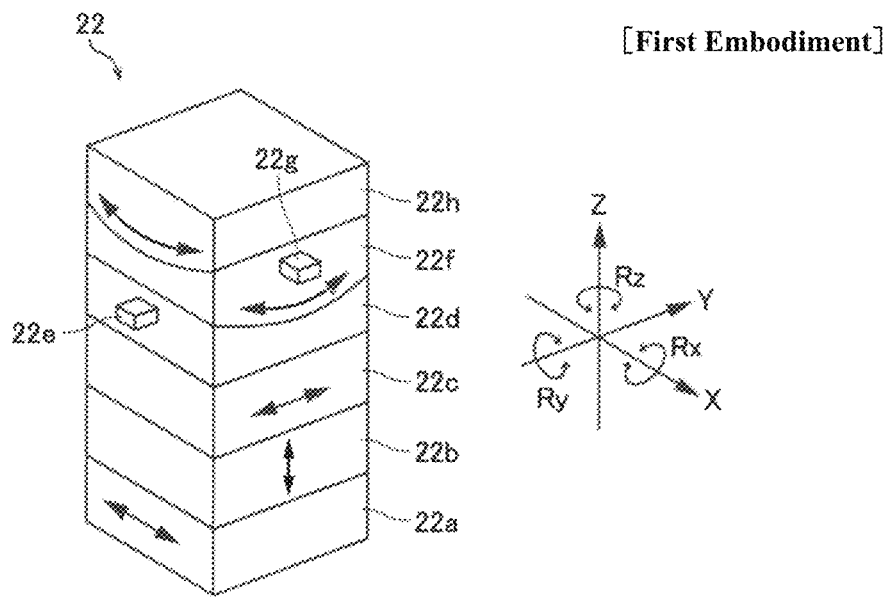
FIG. 3 is a diagram for explaining a configuration of a grating position adjustment mechanism of the X-ray phase imaging apparatus according to the first embodiment.

As shown in FIG. 3, the grating position adjustment mechanism 22 is configured to move the first grating 31 in the X-direction, the Y-direction, the Z-direction, the rotation direction Rz about the axis of the Z-direction, the rotation direction Rx about the axis of the X-direction, and the rotation direction Ry about the axis of the Y-direction. The grating position adjustment mechanism 22 includes an X-direction linear motion mechanism 22a, a Z-direction linear motion mechanism 22b, a Y-direction linear motion mechanism 22c, a linear motion mechanism connecting portion 22d, a stage support portion drive portion 22e, a stage support portion 22f, a stage drive portion 22g, and a stage 22h.

The X-direction linear motion mechanism 22a, the Z-direction linear motion mechanism 22b, and the Y-direction linear motion mechanism 22c are configured to be movable in the X-direction, the Z-direction, and the Y-direction, respectively. The X-direction linear motion mechanism 22a, the Z-direction linear motion mechanism 22b, and the Y-direction linear motion mechanism 22c include, for example, a stepping motor. The grating position adjustment mechanism 22 is configured to move the first grating 31 in the X-direction, the Z-direction, and the Y-direction by the operation of the X-direction linear motion mechanism 22a, the Z-direction linear motion mechanism 22b, and the Y-direction linear motion mechanism 22c, respectively.

The stage support portion 22f supports the stage 22h for mounting (or holding) the first grating 31 in the Z2-direction. The stage drive portion 22g is configured to reciprocate the stage 22h in the X-direction direction. The bottom portion of the stage 22h is formed in a convex curved surface shape toward the stage support portion 22f and is configured to rotate about the axis line (Ry-direction) of the Y-direction by being reciprocated in the X-direction. The stage support portion drive portion 22e is configured to reciprocate the stage support portion 22f in the Y-direction. Further, the linear motion mechanism connecting portion 22d is provided on the X-direction linear motion mechanism 22a so as to be rotatable about the axis line (Ry-direction) of the Z-direction. The bottom of the stage support portion 22f is formed in a convex curved surface shape toward the linear motion mechanism connecting portion 22d and is configured to be rotated about the axis line (Rz-direction) of the X-direction by being reciprocated in the Y-direction direction. The grating position adjustment mechanism 22 may have a mechanism for holding the first grating 31, such as e.g., a chucking mechanism and a hand mechanism.

As shown in FIG. 1, the subject moving mechanism 23 is configured to mount or hold a subject P. The subject moving mechanism 23 is configured to move a subject P in the X-direction by the control of the control unit 21a in a state in which the subject P is placed on or held. That is, in the first embodiment, it is configured such that the imaging system 10 and the subject P can be relatively moved. Although FIG. 1 shows that the subject moving mechanism 23 moves between the first grating 31 and the second grating 32 in the X-direction, the subject moving mechanism 23 may move between the first grating 31 and the third grating 33 in the X-direction.

With the above-described configuration, the X-ray phase imaging apparatus 100 is configured to generate a phase-contrast image 51 (see FIG. 4) based on images acquired by performing imaging while moving the subject P in the X-direction. The generation of the phase-contrast image 51 will be described in detail later.

Figure 5:
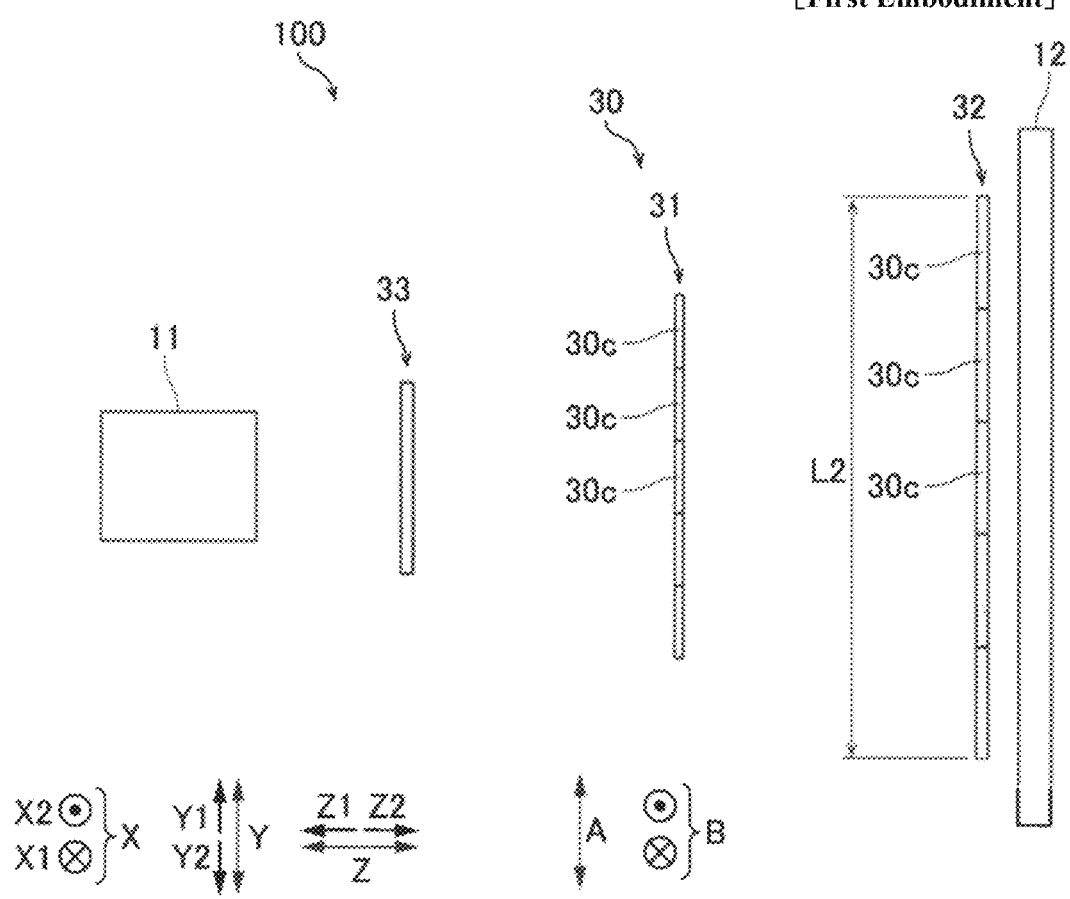
FIG. 5 is a diagram for explaining a grating composed of a plurality of grating portions in the X-ray phase imaging apparatus according to the first embodiment.

Here, in the first embodiment, as shown in FIG. 5, the first grating 31 and the second grating 32 are each composed of a plurality of grating portions 30c arranged side by side along the Y-direction. Specifically, the plurality of grating portions 30c is linearly arranged so as to be adjacent to each other along the Y-direction. For example, the plurality of grating portions 30c is fixed to a grating holding member (not shown) so as to be linearly arranged so as to be adjacent to each other along the Y-direction. As a result, the length L2 of the second grating 32 in the Y-direction is larger than the length L1 in the X-direction. Note that the relation between the length of the first grating 31 in the Y-direction and the length in the X-direction is the same. In the X-ray phase imaging apparatus 100, since the extending direction (B-direction) of the grating 30 coincides with the direction (Y-direction) in which the plurality of grating portions 30c are arranged side by side, the angles of the X-rays entering from the X-ray tube 11 are substantially equal in any of the plurality of grating portions 30c arranged side by side in the Y-direction.

Figure 6:
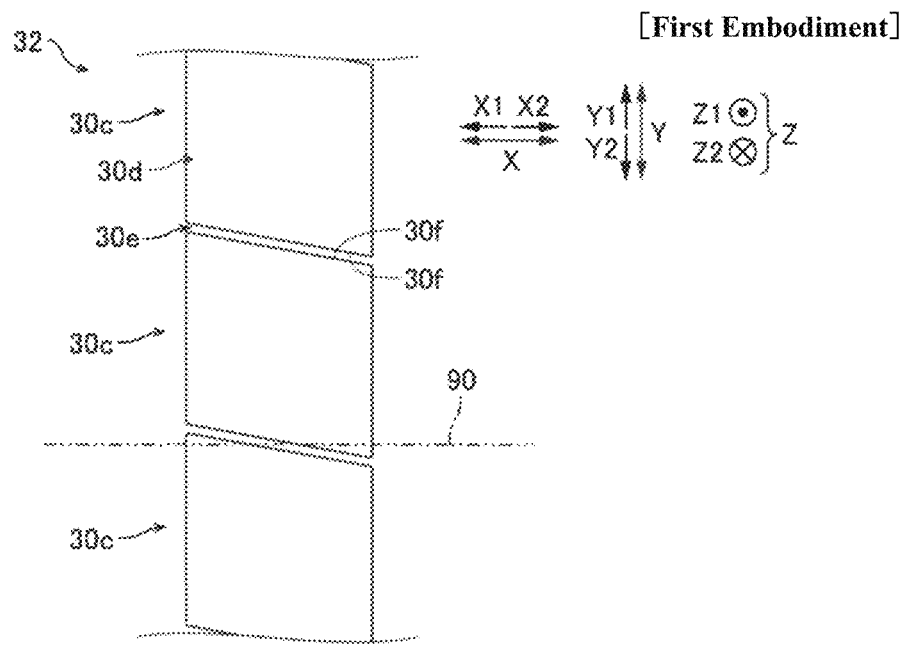
FIG. 6 is a diagram for explaining a plurality of grating portions of the grating in the X-ray phase imaging apparatus according to the first embodiment.
Figure 7:
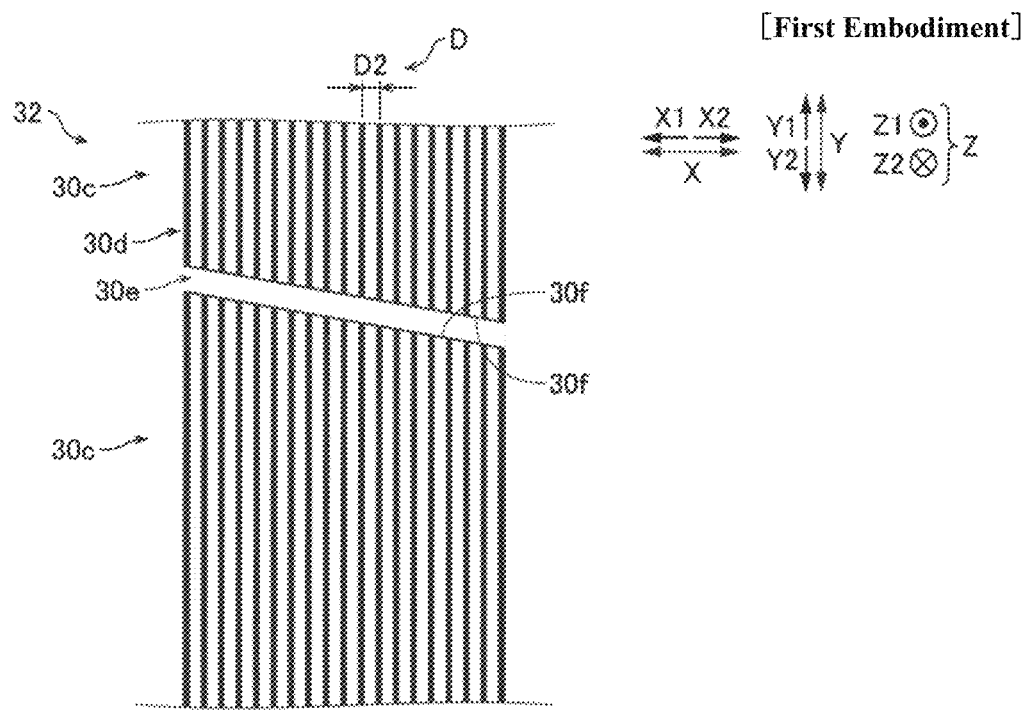
FIG. 7 is a diagram for explaining a gap region formed between a plurality of grating portions in the X-ray phase imaging apparatus according to the first embodiment.

In the first embodiment, as shown in FIG. 6, the plurality of grating portions 30c are configured such that adjacent grating portions 30c overlap each other when viewed in the X-direction. More specifically, the plurality of grating portions 30c are configured such that adjacent grating portions 30c overlap each other when viewed in the X-direction so that at least the grating region 30d is included in the X-direction over the entire Y-direction. Note that in FIG. 6, only the second grating 32 is shown as an example of a grating 30 composed of a plurality of grating portions 30c, but the configuration of the first grating 31 is also the same.

Specifically, each of the plurality of grating portions 30c is formed in a polygonal shape when viewed in the Z-direction. A plurality of parallelogram-shaped grating portions 30c is arranged side by side along the Y-direction, so that a gap region 30e sandwiched by the grating regions 30d is formed between the plurality of grating portions 30c. Note that in FIG. 7, an example is shown in which the spacing of the gap region 30e is larger than the grating pitch D2(D).

The plurality of grating portions 30c is arranged so that the sides 30f of the plurality of grating portions 30c adjacent to each other in the Y-direction includes portions extending in a direction intersecting with the X-direction when viewed in the Z-direction. In the first embodiment, the entire sides 30f are arranged so as to extend in a direction intersecting with the X-direction. In addition, the plurality of grating portions 30c is arranged such that the sides 30f adjacent to each other in the Y-direction are substantially parallel to each other when viewed in the Z-direction. The sides 30f adjacent in the Y-direction extend linearly in a direction intersecting with the X-direction when viewed in the Z-direction.

With the above-described configuration, each of the sides 30f of the plurality of grating portions 30c adjacent in the Y-direction is in a state of extending in a direction intersecting with the XZ-plane 90. As a result, the Y2 side of the grating portion 30c arranged on the Y1 side and the Y1 side of the grating portion 30c arranged on the Y2 side of the plurality of grating portions 30c adjacent in the Y-direction overlap when viewed in the X-direction. The angle at which the side 30f intersecting with the XZ-plane 90 is, for example, less than 45 degrees.

In the first embodiment, the adjacent grating portions 30c overlap each other when viewed in the X-direction so that at least one period D4 (see FIG. 7) of the moiré fringe 40 (see FIG. 8) is included in the X-direction.

Figure 8:
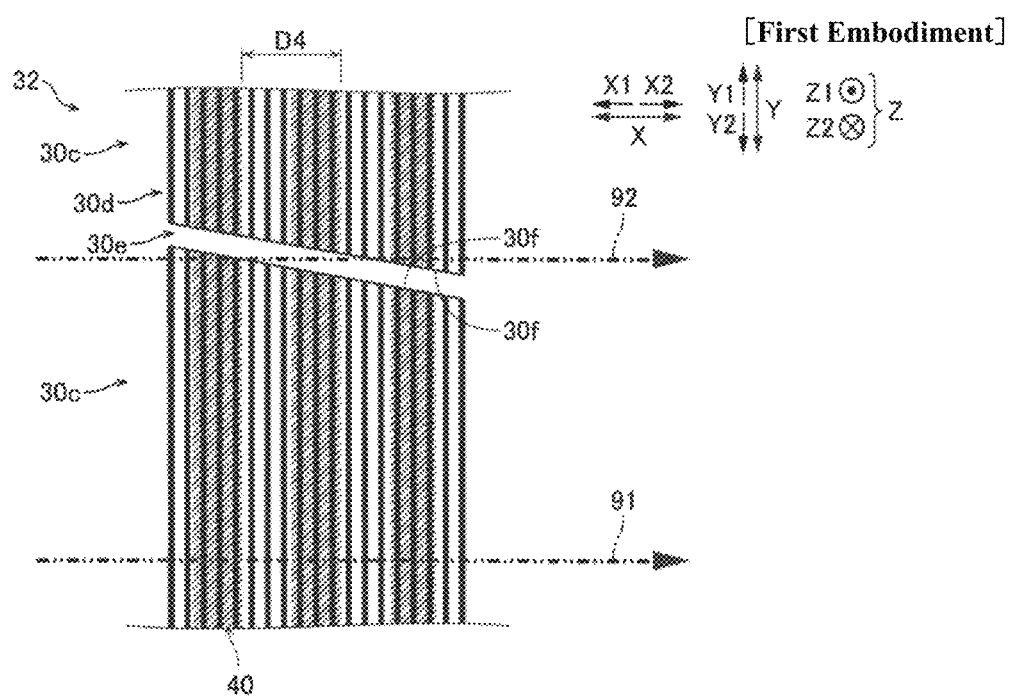
FIG. 8 is a diagram showing a moiré fringe generated at a position of a second grating in the X-ray phase imaging apparatus according to the first embodiment.

More specifically, as shown in FIG. 8, the X-ray phase imaging apparatus 100 is configured to perform imaging while relatively moving the subject P and the imaging system 10 in a state in which a moiré fringe 40 is generated so that at least one period D4 is included in the X-direction in which the subject P and the imaging system 10 are relatively moved. Further, the X-ray phase imaging apparatus 100 is configured to generate the moiré fringe 40 substantially aligned in the X-direction when viewed in the Z-direction in any of the plurality of grating portions 30c arranged side by side along the Y-direction. This allows the subject P to pass through the moiré fringe 40 so as to include at least one period D4 in the X-direction, not only when (each portion of) the subject P moves on the line 91 that does not include the gap region 30e, but also when it moves on the line 92 that includes the gap region 30e when the subject P and the imaging system 10 are relatively moved in the X-direction. In the embodiment shown in FIG. 8, the moiré fringe 40 for approximately three periods is included in the X-direction on the line 91, and the moiré fringe 40 for approximately one period is included in the X-direction on the line 92.

Generation of Phase-Contrast Image

With referring to FIG. 9 to FIG. 15, the generation of a phase-contrast image 51 (see FIG. 4) in the X-ray phase imaging apparatus 100 according to the first embodiment will be described in detail.

In the first embodiment, the image processing unit 21b is configured to generate a phase-contrast image 51 (see FIG. 4) on the basis of a plurality of images (subject images) 52 (see FIG. 9) acquired on the basis of signals detected by the detection unit 12 by performing imaging while moving the subject P in the X-direction (performing imaging while relatively moving the subject P and the imaging system 10).

Figure 9:
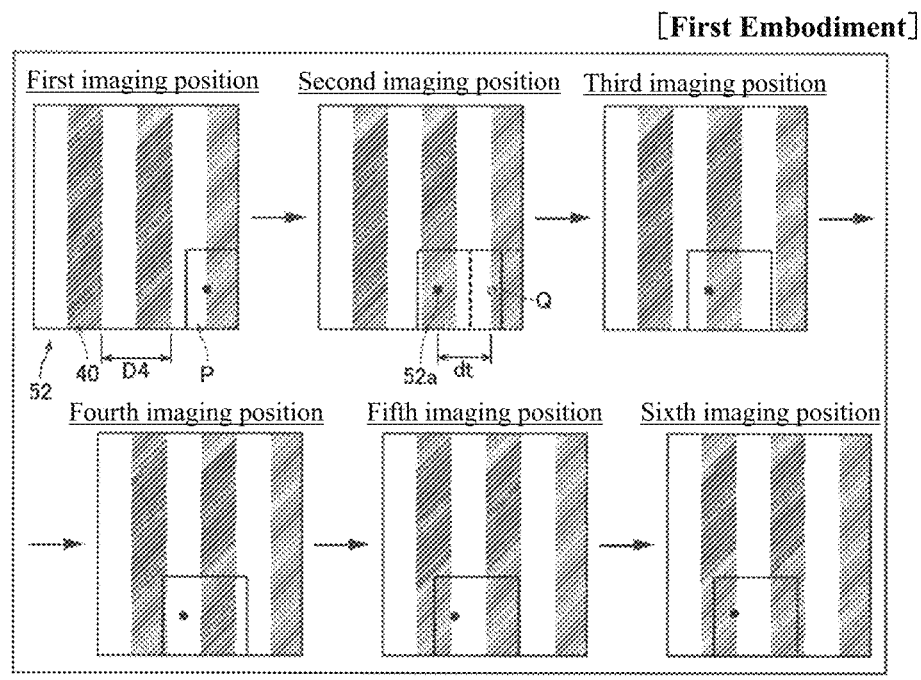
FIG. 9 is a diagram showing a plurality of images (subject images) captured by the X-ray phase imaging apparatus according to the first embodiment.

Specifically, as shown in FIG. 9, the X-ray phase imaging apparatus 100 is configured to perform imaging while moving the subject P in the X-direction in a state in which the moiré fringe 40 is generated. Note that in FIG. 9, a plurality of (six) subject images 52 captured at the first to sixth imaging positions are shown while linearly moving the subject P in the X-direction by the subject moving mechanism 23 (see FIG. 1). FIG. 9 shows a change in the position of the pixel 52a among the pixels obtained by imaging the subject P in the plurality of subject images 52.

The control unit 21a (see FIG. 1) moves the subject P by a predetermined movement amount dt by inputting a command value relating to a movement amount for arranging the subject P at each imaging position to the subject moving mechanism 23 (see FIG. 1). For example, when the subject moving mechanism 23 includes a stepping motor as a driving source, the command value for the moving distance dt is the number of pulses inputted to the subject moving mechanism 23. Note that in the subject image 52 at the second imaging position of FIG. 9, the position of the subject P at the first imaging position is illustrated by a broken line in order to make it easier to grasp the moving distance dt of the subject P.

As described above, by performing imaging while moving the subject P by the subject moving mechanism 23 (see FIG. 1), the moiré fringe 40 and the subject P can be relatively moved. As a result, the image processing unit 21b (see FIG. 1) can generate the phase-contrast image 51 (see FIG. 4) based on the subject images 52 captured at the respective imaging positions (first to sixth imaging positions). Note that in the first embodiment, it is configured such that the subject P is moved by the subject moving mechanism 23 by at least one period D4 of the moiré fringe 40.

Here, when imaging is performed while moving the subject P with respect to the moiré fringe 40, unlike when imaging is performed by translating the grating, the phase value of the pixel in each image (the subject image 52) cannot be obtained directly. Therefore, in the first embodiment, the image processing unit 21b (see FIG. 1) is configured to generate a phase-contrast image 51 based on the pixel value of each pixel 52a in the plurality of subject images 52 and the phase information 41 (see FIG. 10) of the moiré fringe 40 generated in the plurality of subject images 52.

Figure 10:
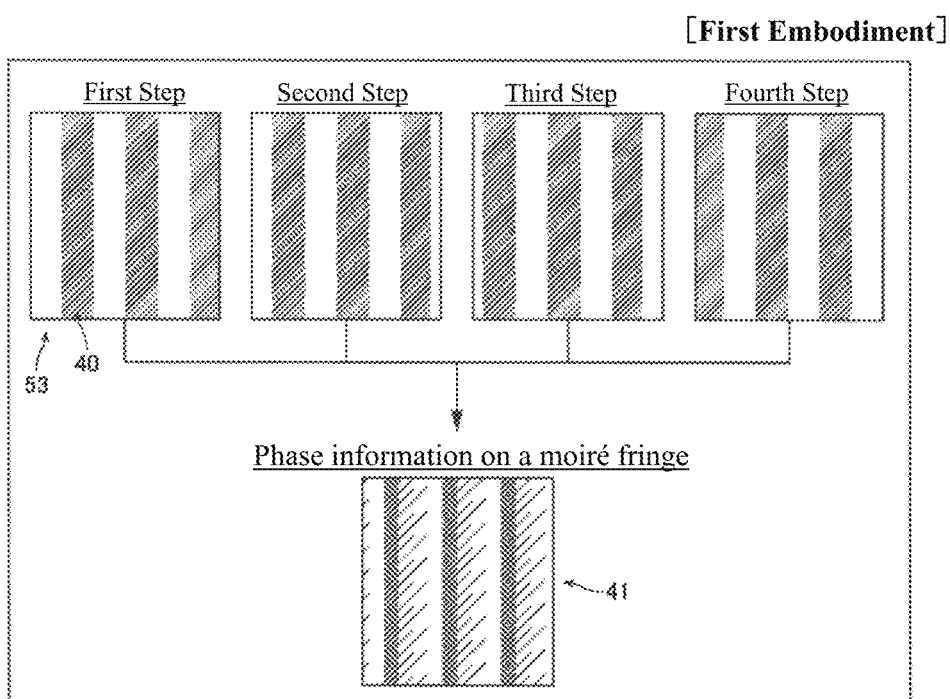
FIG. 10 is a diagram for explaining obtaining the phase information on the moiré fringe in the X-ray phase imaging apparatus according to the first embodiment.

Specifically, as shown in FIG. 10, in the X-ray phase imaging apparatus 100, the image processing unit 21b (see FIG. 1) is configured to acquire the phase information 41 of the moiré fringe 40. That is, the X-ray phase imaging apparatus 100 acquires the moiré fringe image 53 of each Step (translationally moved position) by translationally moving the first grating 31 (see FIG. 1) by the grating position adjustment mechanism 22 (see FIG. 1). The moiré fringe image 53 is an image of the moiré fringe 40 generated on the detecting surface of the detection unit 12 (see FIG. 1) by translationally moving the first grating 31, and is an image of a striped pattern with bright and dark pixel values of the moiré fringe 40.

The image processing unit 21b (see FIG. 1) is configured to acquire the phase information 41 on the moiré fringe 40 based on each moiré fringe image 53. The phase information 41 on the moiré fringe 40 is an image of a striped pattern in which the change of the phase value of the moiré fringe 40 is repeated every one period D4. That is, the phase information 41 on the moiré fringe 40 is an image in which the change of the phase value of the moiré fringe 40 from −π to π is illustrated in a striped pattern. The phase information 41 of the moiré fringe 40 may be in the range of −π to π or in the range of 0 to 2π as long as the range is 2π.

The image processing unit 21b (see FIG. 1) is configured to associate the pixel value of each pixel of the subject P in the plurality of subject images 52 with the phase value of the moiré fringe 40 in each pixel based on the plurality of subject images 52 acquired by performing imaging while relatively moving the subject P and the imaging system 10 and the phase information 41 of the moiré fringe 40 generated in the plurality of subject images 52. The image processing unit 21b is configured to generate the phase-contrast image 51 by performing the alignment of the pixels at the same position of the subject P in the plurality of subject images 52 based on the position information on the pixels at the same position of the subject P in the plurality of subject images 52 and the pixel value of each pixel associated with the phase value.

In the X-ray phase imaging apparatus 100, the image processing unit 21b (see FIG. 1) is configured to create position calibration data and perform alignment of pixels at the same position of the subject P in the plurality of subject images 52 using the created position calibration data.

Figure 11:
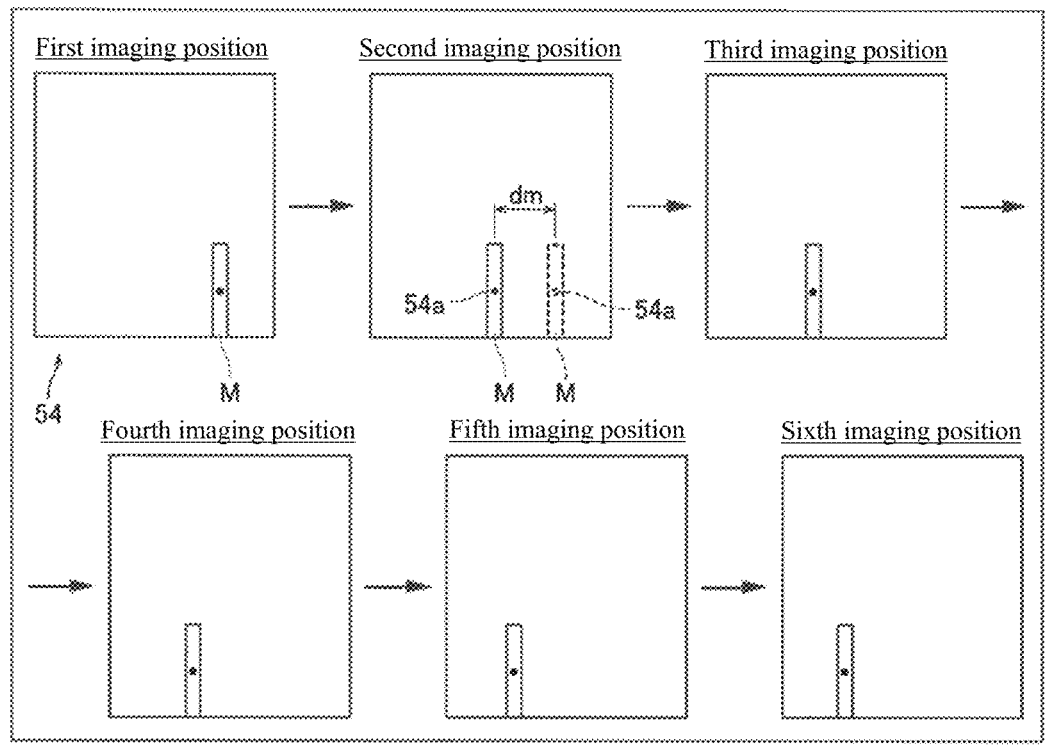
FIG. 11 is a diagram showing a plurality of position calibration images imaged by the X-ray phase imaging apparatus according to the first embodiment.

Specifically, as shown in FIG. 11, the image processing unit 21b (see FIG. 1) is configured to generate position calibration data used for aligning pixels at the same position of the subject P in the plurality of subject images 52 (see FIG. 9) based on the plurality of position calibration images 54 captured while relatively moving the label M and the imaging system 10 (see FIG. 1). The label M may be anything as long as it absorbs X-rays. The label M includes, for example, a wire. FIG. 11 shows the position calibration image 54 captured at first to sixth imaging positions while moving the label M in the X-direction by the subject moving mechanism 23 (see FIG. 1). In addition, in the examples shown in FIG. 11, the movement amount dm of the label M is acquired by focusing on the pixel 54a among the pixels in which the label M is imaged.

The position calibration data is created based on a command value relating to a movement amount inputted to the subject moving mechanism 23 when relatively moving the label M and the imaging system 10 by the subject moving mechanism 23 (see FIG. 1) and an actual movement amount dm of the label M in the position calibration image 54 when the label M and the imaging system 10 are relatively moved based on the command value. More specifically, the position calibration data is created by acquiring an approximate expression indicating the relation between the command value and the movement amount dm of the label M based on the position of the pixels at the same position of the label M in the plurality of position calibration images 54.

Figure 12:
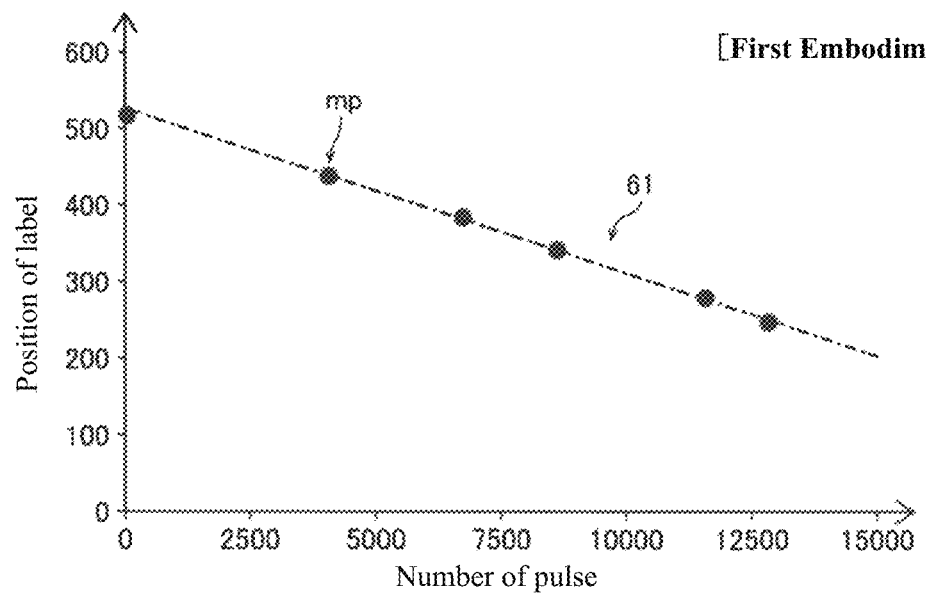
FIG. 12 is a diagram for explaining obtaining the position calibration data in the X-ray phase imaging apparatus according to the first embodiment.

Specifically, as shown in FIG. 12, the control unit 21a (see FIG. 1) obtains an approximate expression by linearly fitting the plots mp shown in the graph 61. FIG. 12 is a graph 61 in which the vertical axis represents the position of the label M in the position calibration image 54 and the horizontal axis represents command values when the label M is moved.

Figure 13:
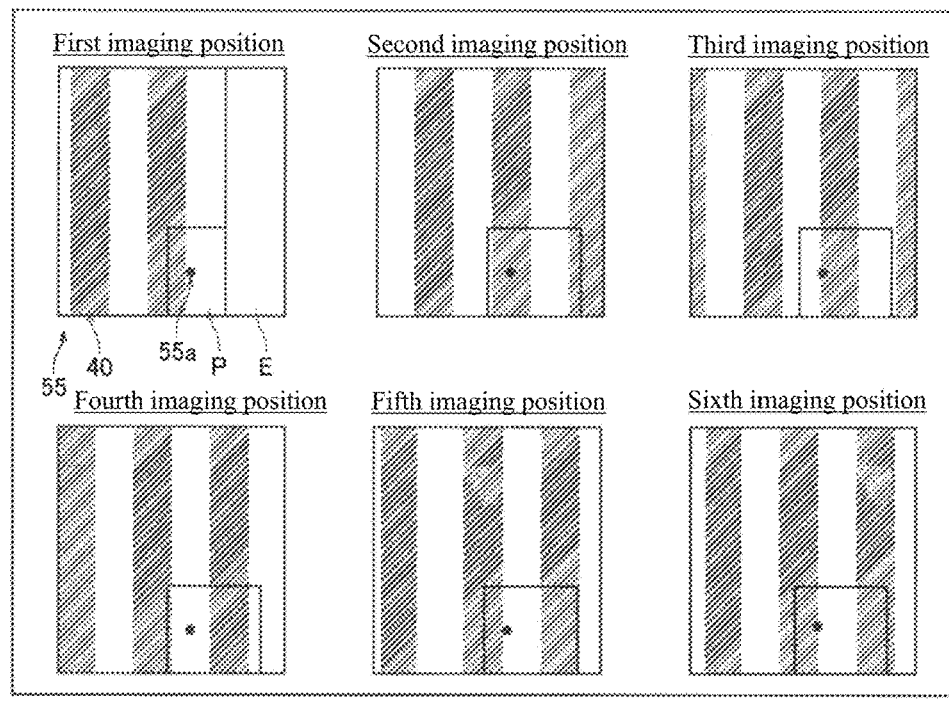
FIG. 13 is a diagram for explaining the alignment of each pixel at the same position of a subject in a plurality of images captured by the X-ray phase imaging apparatus according to the first embodiment.

Then, as shown in FIG. 13, the image processing unit 21b (see FIG. 1) acquires the position in each subject image 52 (see FIG. 9) of the pixel at the same position of the subject P using the position calibration data, and performs the alignment of the pixels in each subject image 52. FIG. 13 shows a subject image 55 in which the subject images 52 at the first to sixth imaging positions are aligned so that the subject P at the second imaging position is stationary. Further, in FIG. 13, since the whole of the subject P in the X-direction is not reflected in the image captured by arranging the subject P at the first imaging position, a blank area E is generated in the subject image 55 after the alignment. That is, when attention is paid to the pixel 55a in the subject images 55 after the alignment, it is understood that the moiré fringe 40 is moved with respect to the pixel 55a.

In addition, in the X-ray phase imaging apparatus 100, the image processing unit 21b (see FIG. 1) is configured to perform alignment using position calibration data also for the phase information 41 of the moiré fringe 40 in order to acquire the phase value of the moiré fringe 40 in each pixel of each subject image 55 after the alignment.

Figure 14:
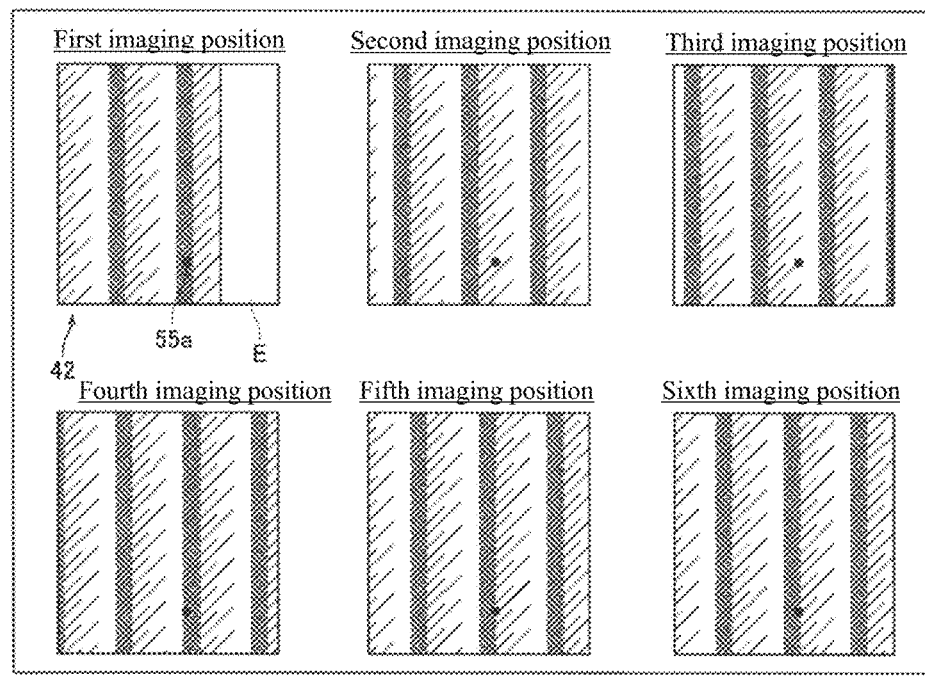
FIG. 14 is a diagram for explaining the alignment of the phase information on the moiré fringe in the X-ray phase imaging apparatus according to the first embodiment.

More specifically, as shown in FIG. 14, the image processing unit 21b (see FIG. 1) is configured to align the position of the phase information 42 at each imaging position by performing the same converting process as that performed when converting into an image in which the subject P is still also for the phase information 42 of the moiré fringe 40.

FIG. 14 shows the phase information 42 after the phase information 41 of the moiré fringe 40 shown in FIG. 10 is aligned using the position calibration data. In addition, in the example shown in FIG. 14, the position corresponding to the position of the pixel 55a of each subject image 55 after the alignment is illustrated by a point 55b. That is, the position of the pixel at each imaging position and the position of the phase value of the moiré fringe 40 in the phase information 42 after the alignment are associated with each other in a one-to-one relation.

Figure 15:
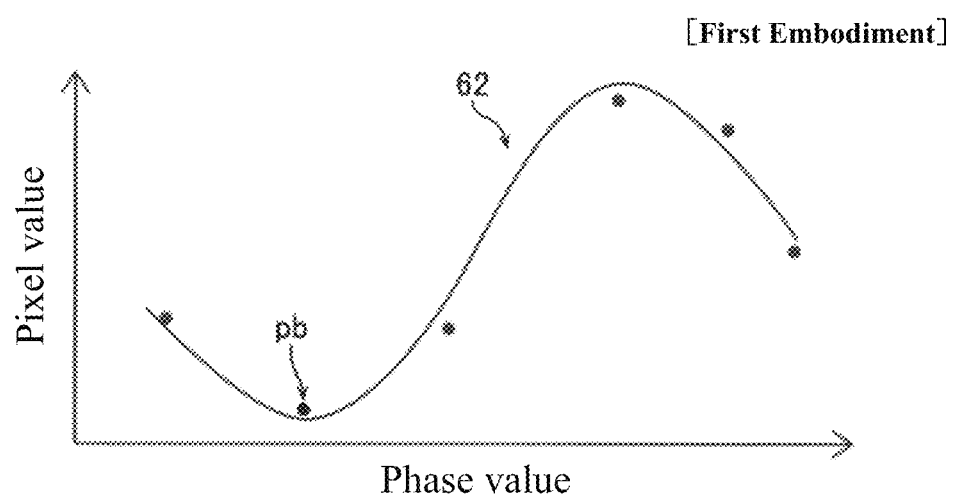
FIG. 15 is a diagram showing an intensity signal curve obtained by associating each phase value and each pixel value of each pixel of a plurality of images captured by the X-ray phase imaging apparatus according to the first embodiment in a one-to-one relation.

As shown in FIG. 15, the image processing unit 21b (see FIG. 1) acquires the intensity signal curve 62 of the pixel value in which the respective phase values of the pixels at the same position of the subject P in the plurality of subject images 55 and the respective pixel values are associated with each other in a one-to-one relation, using the respective subject images 56 after the alignment and the phase information 42.

Note that in the intensity signal curve 62 shown in FIG. 15, the horizontal axis represents phase values, and the vertical axis represents pixel values. FIG. 15 shows an intensity signal curve 62 obtained by acquiring plots pb based on the pixel value in each pixel 55a of the plurality of subject images 55 and the phase value of each point 55b corresponding to the pixel 55a of the subject image 55 in the plurality of phase information 42 and fitting the plots pb with a sine wave. Note that the blank area E shown in FIG. 13 is not sampled in FIG. 15 because there is no phase information 42 of the moiré fringe 40. The image processing unit 21b is configured to generate the phase-contrast image 51 (see FIG. 4) based on the acquired intensity signal curve 62.

Phase-contrast Image Generation Flow

Figure 16:
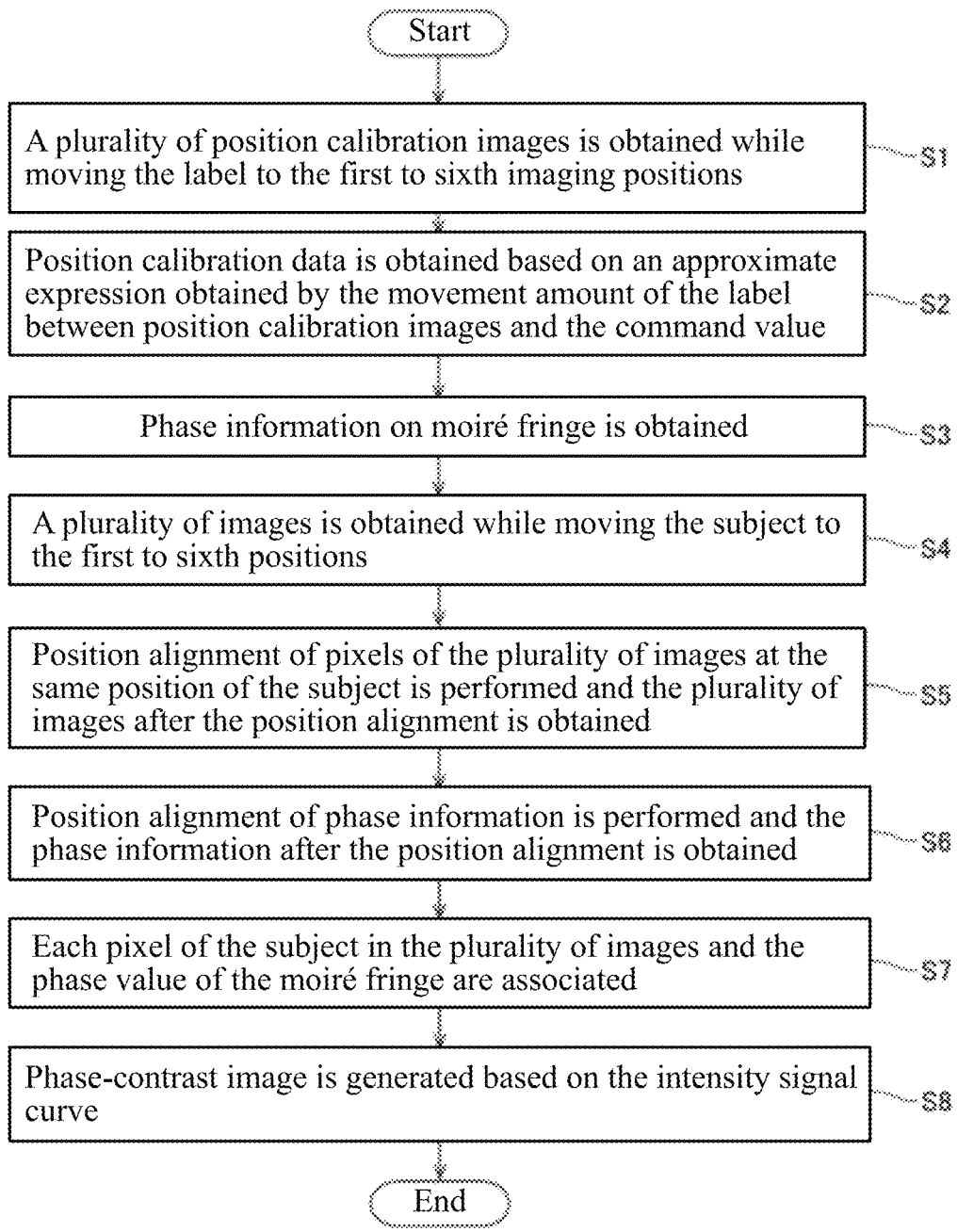
FIG. 16 is a flowchart for explaining the generation process of the phase-contrast image in the X-ray phase imaging apparatus according to the first embodiment.

Next, with reference to FIG. 16, a flow of generating the phase-contrast image 51 (see FIG. 4) by the X-ray phase imaging apparatus 100 according to the first embodiment will be described.

First, in Step S1, the image processing unit 21b acquires a plurality of position calibration images 54 while moving the label M to the first to sixth imaging positions by the subject moving mechanism 23 under the control of the control unit 21a.

Next, in Step S2, the control unit 21a obtains an approximate expression based on the movement amount dm of the label M and the command value. The control unit 21a acquires the position calibration data based on the slope of the acquired approximate expression.

Next, in Step S3, the image processing unit 21b acquires phase information 41 of the moiré fringe 40.

Next, in Step S4, the image processing unit 21b acquires a plurality of subject images 52 while relatively moving the subject P and the imaging system 10 by the subject moving mechanism 23 under the control of the control unit 21a.

Next, in Step S5, the image processing unit 21b performs alignment of pixels at the same position of the subject P in the plurality of subject images 52 and acquires a plurality of subject images 55.

Next, in Step S6, the image processing unit 21b performs alignment of the phase information 41 and acquires a plurality of phase information 42.

Next, in Step S7, the image processing unit 21b associates the pixel of the subject P in the plurality of subject images 55 with the phase value of the moiré fringe 40.

Next, in Step S8, the image processing unit 21b generates the phase-contrast image 51 based on the intensity signal curve 62, and ends the process.

It should be noted that either the acquisition processing of the position calibration data in Step S1 and Step S2 or the acquisition processing of the phase information 41 of the moiré fringe 40 in Step S3 may be performed first. That is, the acquisition processing of the position calibration data may be performed at any time as long as it is prior to the alignment of the pixels in the plurality of subject images 52. The acquisition processing of the phase information 41 of the moiré fringe 40 may be performed at any time prior to the process of aligning the phase information 42.

Effects of Embodiment 1

In the device of the first embodiment, the following effects can be obtained.

In the first embodiment, as described above, at least one of the plurality of gratings 30 (the first grating 31 and the second grating 32) is composed of the plurality of grating portions 30c arranged side by side along a third direction (Y-direction) perpendicular the first direction (X-direction) in which the subject P or the imaging system 10 is moved by the subject moving mechanism 23 and the second direction (Z-direction) in which the X-ray tube 11, the detection unit 12, and the plurality of gratings 30 are arranged, and the plurality of grating portions 30c are arranged such that adjacent grating portions 30c overlap each other when viewed in the first direction.

As a result, it is possible to suppress the occurrence of a portion in which the subject P hardly passes through the grating 30 in the third direction in which the plurality of grating portions 30c is arranged side by side when performing imaging while relatively moving the subject P and the imaging system 10 in the first direction in the grating 30 (the first grating 31 and the second grating 32) composed of the plurality of grating portions 30c. As a result, in a configuration in which imaging is performed while relatively moving the subject P and the imaging system 10, it is possible to increase the area in a direction perpendicular to the direction (X-direction) in which the subject P and the imaging system 10 are relatively moved while suppressing the occurrence of a portion in which the subject P cannot be imaged due to the occurrence of a portion in which the subject hardly passes through the grating.

Further, in the first embodiment, as described above, the image processing unit 21b is configured to generate the phase-contrast image 51 based on the pixel values of the respective pixels in the plurality of images and the phase information 41 of the moiré fringes 40 generated in the plurality of images (subject images 52), and the plurality of grating portions 30c are arranged so that adjacent grating portions 30c overlap each other when viewed in the first direction so that at least one period D4 of the moiré fringes 40 is included in the first direction (X-direction) over the entire third direction (Y-direction).

As a result, since the subject P can pass (can be imaged) at least for one period D4 of the moiré fringe 40 over the entire third direction (Y-direction), it becomes possible to suppress the occurrence of a portion in which the phase-contrast image 51 based on the phase information 41 cannot be generated due to the occurrence of a portion in which the image of one period D4 of the moiré fringe 40 cannot be captured.

Further, in the first embodiment, as described above, the gap region 30e sandwiched by the grating regions 30d is formed between the plurality of grating portions 30c arranged side by side along the third direction (Y-direction), and the plurality of grating portions 30c are arranged such that adjacent grating portions 30c overlap each other when viewed in the first direction so that at least the grating region 30d is included in the first direction (X-direction) over the entire third direction.

Thereby, by arranging the plurality of grating portions 30c side by side along the third direction, even when the gap region 30e is formed between the plurality of grating portions 30c due to an error or the like at the time of manufacturing the grating, it is possible to reliably suppress the occurrence of the grating portion 30c in which the subject P hardly passes through in the third direction in which the plurality of grating portions 30c is arranged side by side. Therefore, it is possible to effectively suppress the generation of a portion where the subject P cannot be imaged.

In the first embodiment, as described above, the plurality of grating portions 30c are formed in a polygonal shape as viewed in the second direction (Z-direction), and the adjacent sides 20f of the plurality of grating portions 30c arranged adjacent to each other along the third direction (Y-direction) are arranged so as to include the portion extending in a direction intersecting with the first direction (X-direction) as viewed in the second direction, whereby the adjacent grating portions 30c are configured to overlap as viewed in the first direction.

With this, it is possible to easily make the adjacent grating portions 30c overlap each other when viewed in the first direction by the portion extending in a direction intersecting with the first direction when viewed in the second direction between the sides 20f of the plurality of grating portions 30c adjacent in the third direction. Further, since the plurality of grating portions 30c need not be arranged in two or more columns in the first direction as compared with the case in which the plurality of grating portions 30c is arranged in a zigzag shape as viewed in the second direction (Z-direction) in order to cause the adjacent grating portions 30c to overlap as viewed in the first direction, it is possible to suppress the grating 30 from becoming large in size in the first direction.

Further, in the first embodiment, as described above, the plurality of grating portions 30c is arranged such that the sides 30f of the plurality of grating portions 30c adjacent in the third direction arranged adjacent to each other along the third direction (Y-direction) extend across the entire side 30f as viewed in the second direction (Z-direction) in a direction intersecting with the first direction (X-direction).

This makes it possible to lengthen a portion extending in a direction intersecting with the first direction as compared with a case in which only a portion of the sides 30f of the plurality of grating portions 30c adjacent to each other in the third direction extends in a direction intersecting with the first direction as seen from the second direction, and therefore, it is possible to more easily make the adjacent grating portions 30c overlap as seen from the first direction.

Further, in the first embodiment, as described above, the plurality of grating portions 30c is arranged such that the sides 30f adjacent in the third direction (Y-direction) are substantially parallel to each other when viewed in the second direction (Z-direction).

With this, it is possible to suppress the occurrence of a relatively large gap between the sides 30f of the plurality of grating portions 30c adjacent to each other in the third direction as compared with the case in which the sides 30f adjacent to each other in the third direction are not substantially parallel. Therefore, it is possible to more easily make the sides 30f of the plurality of grating portions 30c adjacent to each other in the third direction overlap the grating portion 30c adjacent to each other when viewed in the first direction.

Embodiment 2

Figure 17:
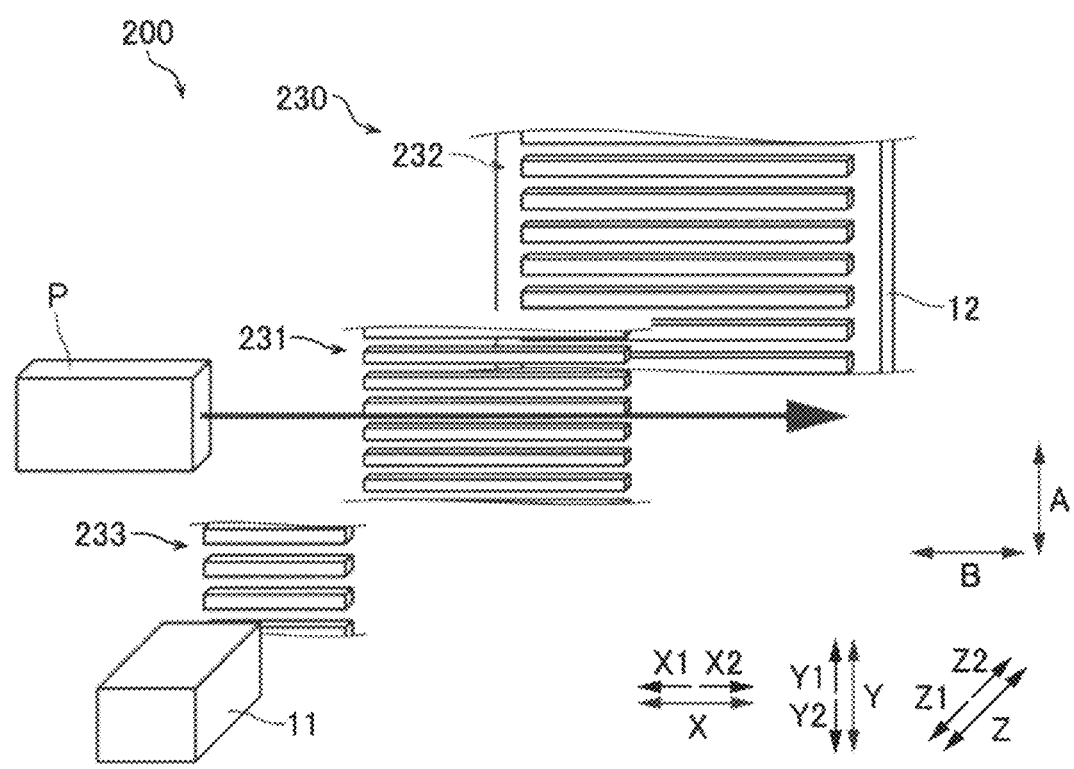
FIG. 17 is a diagram for explaining a configuration of a grating in the X-ray phase imaging apparatus according to a second embodiment.
Figure 18:
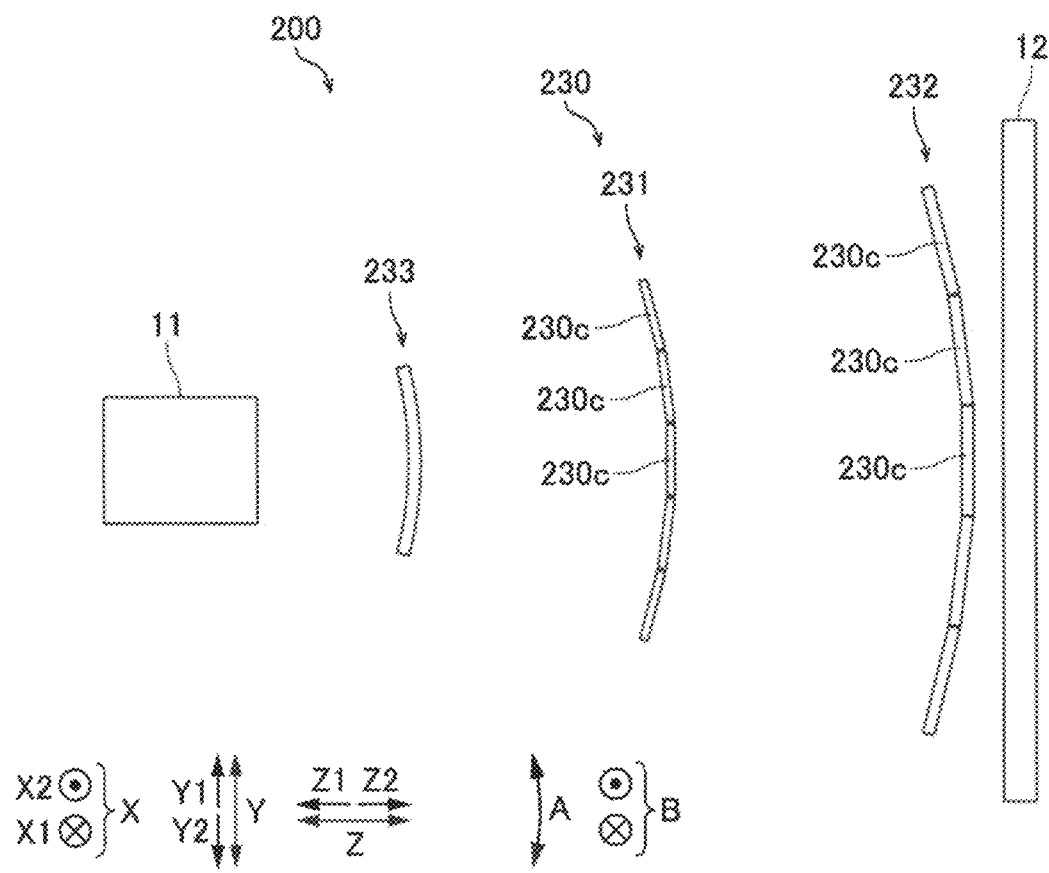
FIG. 18 is a diagram for explaining a grating composed of a plurality of grating portions in the X-ray phase imaging apparatus according to the second embodiment.
Figure 19:
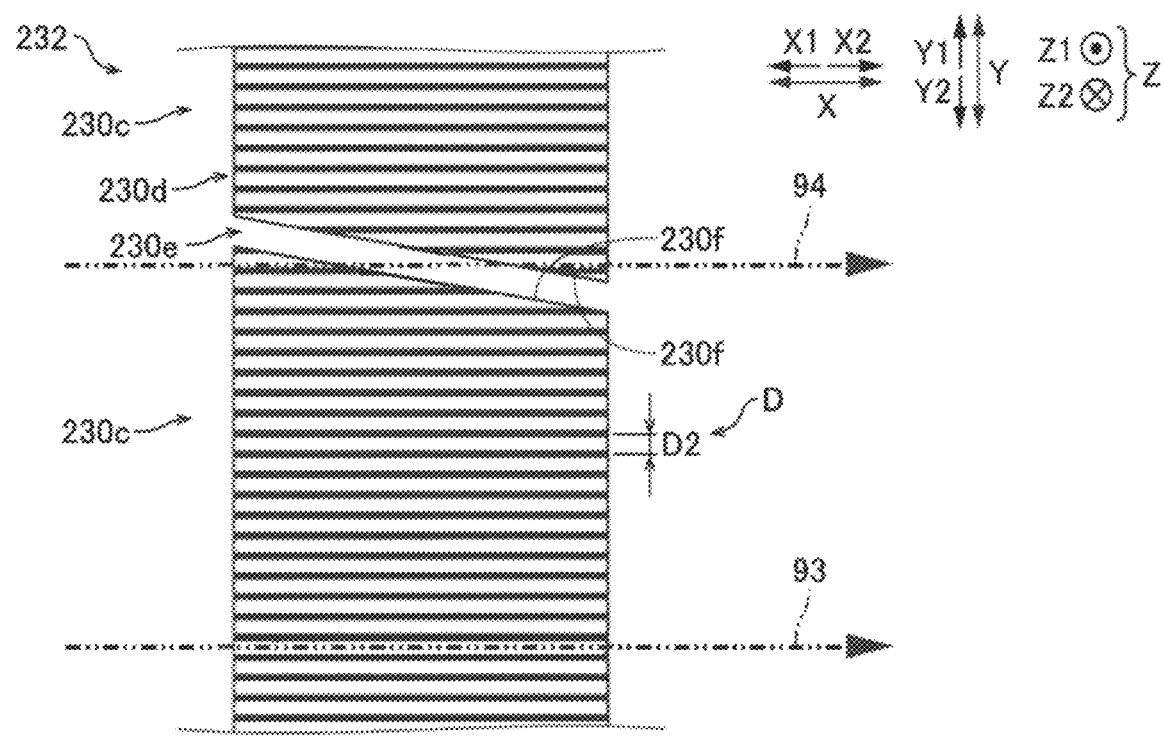
FIG. 19 is a diagram for explaining a gap region formed between a plurality of grating portions in the X-ray phase imaging apparatus according to the second embodiment.

With reference to FIG. 17 to FIG. 19, a second embodiment will be described. This second embodiment is different from the first embodiment which is configured to perform imaging while relatively moving the subject P and the imaging system 10 in the direction of the grating pitch D of the plurality of gratings 30. The second embodiment is configured to perform imaging while relatively moving the subject P and the imaging system 10 in the direction of the extension of the grating 230 of the plurality of gratings 230. Note that in the drawings, the same component as that of the first embodiment is denoted by the same reference symbol.

As shown in FIG. 17, the X-ray phase imaging apparatus 200 according to the second embodiment of this embodiment is provided with a plurality of gratings 230. The plurality of gratings 230 includes a first grating 231, a second grating 232, and a third grating 233. As shown in FIG. 18, the first grating 231 and the second grating 232 are each composed of a plurality of grating portions 230c arranged side by side along the Y-direction. In the second embodiment, the grating pitch direction (A-direction) of the plurality of gratings 230 and the extending direction (B-direction) of the grating 230 of the plurality of gratings 230 are denoted as a Y-direction and an X-direction, respectively. Also note that, in the second embodiment, the Y-direction and the X-direction are examples of the "first direction" and the "third direction" recited in claims, respectively.

As shown in FIG. 19, the plurality of grating portions 230c are arranged such that adjacent grating portions 230c overlap each other when viewed in the X-direction in the same manner as in the first embodiment. Specifically, a gap region 230e sandwiched between the grating regions 230d is formed between the plurality of grating portions 230c.

In FIG. 19, an example is shown in which the spacing of the gap region 230e is larger than the grating pitch D2 (D). The plurality of grating portions 230c is arranged such that the sides 230f of the plurality of grating portions 230c adjacent to each other in the Y-direction extend in a direction intersecting with the X-direction over the entire side 230f as viewed in the Z-direction. Although only the second grating 232 is shown as an example of the grating 230 composed of a plurality of grating portions 230c, the configuration of the first grating 231 is the same.

Here, in the second embodiment, as shown in FIG. 18, the first grating 231 and the second grating 232 each have a plurality of grating portions 230c arranged in an arc shape so as to have a convex arc shape toward the detection unit 12 side (Z2 side) when viewed in the X-direction.

Specifically, in the X-ray phase imaging apparatus 200, the plurality of gratings 230 (the first grating 231, the second grating 232, and the third grating 233) is each configured to have a shape along an arc (not shown) centered on the X-ray tube 11. The first grating 231 and the second grating 232 are each composed of a plurality of grating portions 230c arranged along an arc so as to face the X-ray tube 11. That is, when viewed in the Z-direction, any portion of the grating 230 is arranged so as to face the X-ray tube 11. Note that, in the X-ray phase imaging apparatus 200, any portion of the grating 230 is arranged so as to extend in a direction intersecting with the X-direction over the entire side 230f when viewed in the Z-direction, and is arranged so that any portion of the plurality of grating portions 230c faces toward the X-ray tube 11, so that only cross-sectional portions of the plurality of grating portions 230c adjacent to each other in the Y-direction are opposed to each other (are positioned so as to be twisted with each other).

In the X-ray phase imaging apparatus 200, the subject moving mechanism 23 is configured to move the subject P or the imaging system 10 along the direction (B-direction) in which the gratings of the plurality of gratings 230 extend.

According to the above configuration, as shown in FIG. 19, in the X-ray phase imaging apparatus 200, in the same manner as in the X-ray phase imaging apparatus 100 according to the first embodiment, when the subject P and the imaging system 10 are relatively moved in the X-direction, it is possible to make the subject P pass through the moiré fringes 40 (see FIG. 8) so as to include at least one period D4 (see FIG. 8) in the X-direction not only when (each portion of) the subject P moves on the line 93 that does not include the gap region 230e but also when the subject P moves on the line 94 that includes the gap region 230e.

The rest of the configuration of the X-ray phase imaging apparatus 200 according to the second embodiment is the same as that of the first embodiment.

Effects of Embodiment 2

In the second embodiment, the following effects can be obtained.

In the second embodiment, as described above, the subject moving mechanism 23 is configured to move the subject P or the imaging system 10 along the direction (B-direction) in which the gratings of the plurality of gratings 230 extend, and the plurality of grating portions 230c is arranged side by side along the arc such that at least one of the gratings 230 (the first grating 231 and the second grating 232) composed of the plurality of grating portions 230c has a convex arc shape on the detection unit 12 side (the Z2-side) as viewed in the first direction (X-direction).

This makes it possible to suppress oblique incidence (oblique incidence) of X-rays in all of the plurality of grating portions 230c arranged side by side along the third direction (Y-direction) as compared with when the plurality of grating portions 230c is arranged substantially linearly as viewed in the first direction. As a result, in a third direction in which the grating 230 is increased in size by arranging the plurality of grating portions 230c side by side, it is possible to suppress the occurrence of a portion in which the X-ray dose passing through the grating 230 decreases due to oblique incidence of X-rays and to suppress the occurrence of a portion in which the X-ray dose required for image generation cannot be detected.

The other effects of the second embodiment are the same as those of the first embodiment.

Embodiment 3

Figure 20:
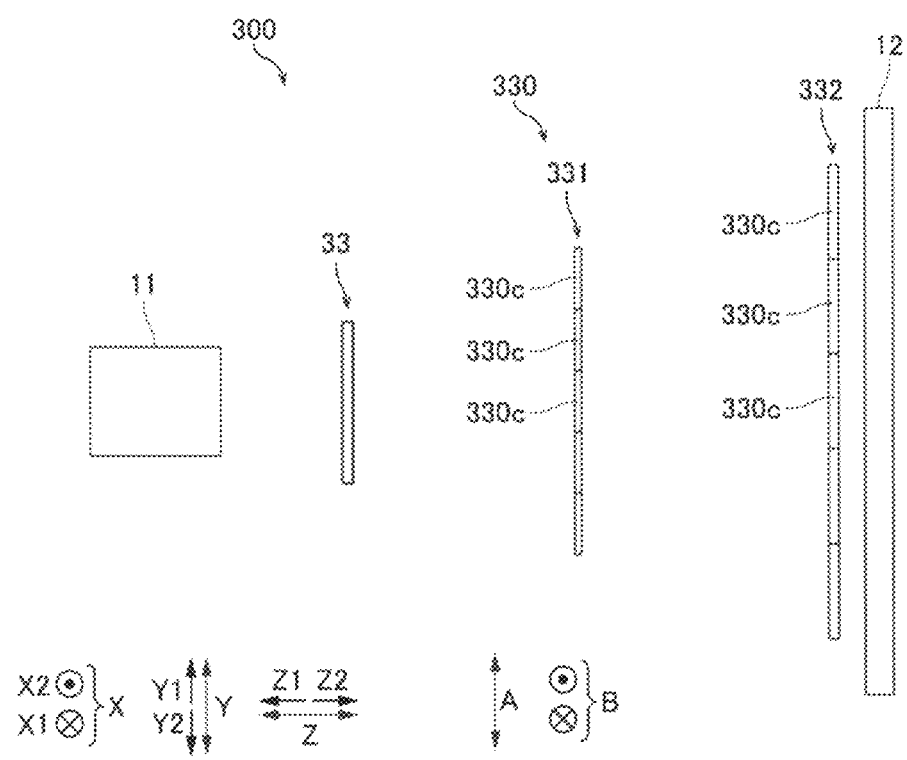
FIG. 20 is a diagram for explaining a grating composed of a plurality of grating portions in the X-ray phase imaging apparatus according to a third embodiment.
Figure 21:
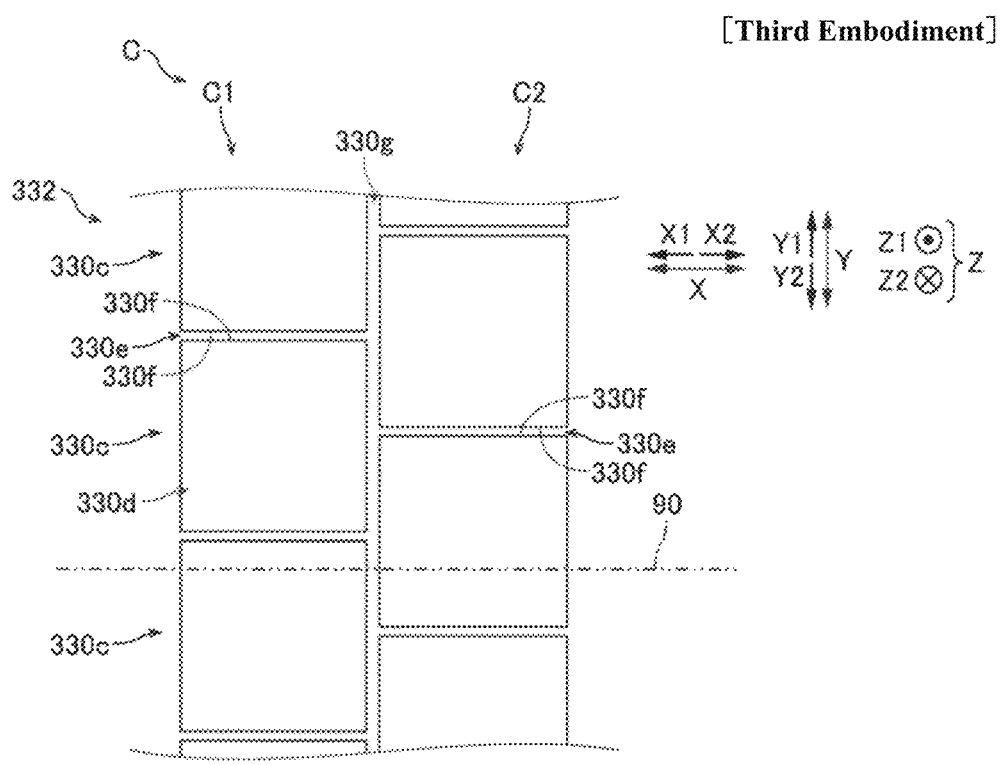
FIG. 21 is a diagram for explaining a plurality of grating portions of the grating in the X-ray phase imaging apparatus according to the third embodiment.
Figure 22:
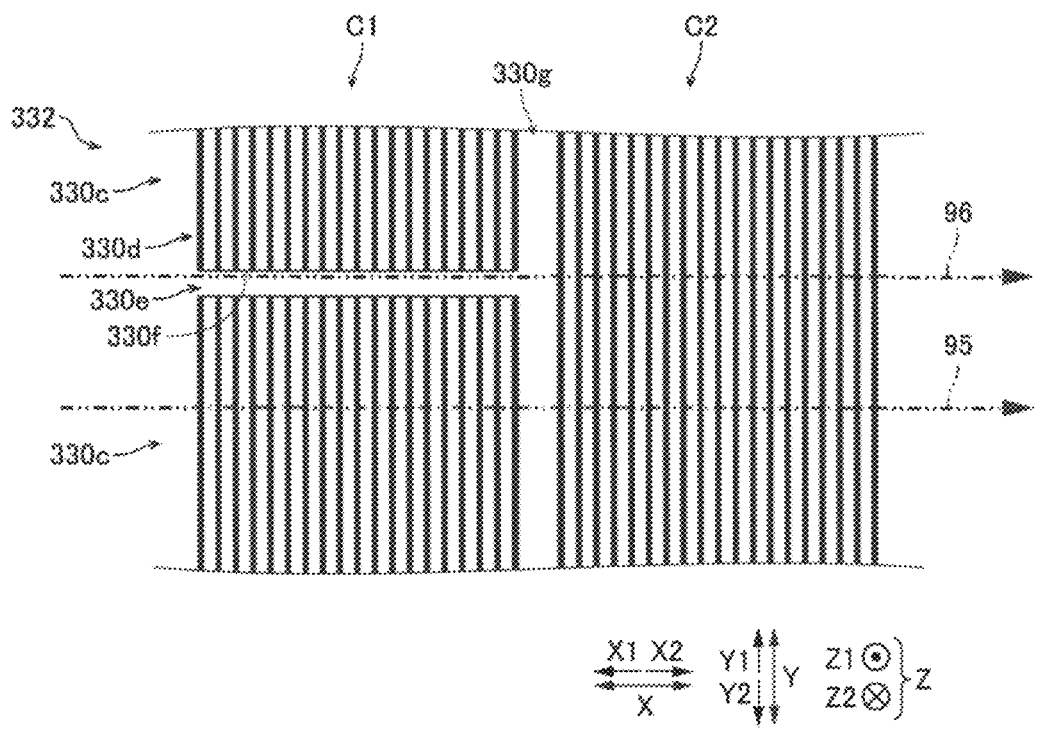
FIG. 22 is a diagram for explaining a gap region formed between a plurality of grating portions in the X-ray phase imaging apparatus according to the third embodiment.

With reference to FIG. 20 to FIG. 22, a third embodiment will be described. This third embodiment is different from the first embodiment in which the sides 30f of the plurality of grating portions 30c adjacent in the Y-direction are configured to include a portion extending in a direction intersecting with the X-direction when viewed in the Z-direction. The third embodiment is configured so that the plurality of grating portions 330c is arranged in a zigzag shape (staggered shape) when viewed in the Z-direction. Note that in the drawings, the same component as that of the first embodiment are denoted by the same reference symbol.

As shown in FIG. 20, the X-ray phase imaging apparatus 300 according to the third embodiment of this embodiment is provided with a plurality of gratings 330. The plurality of gratings 330 includes a first grating 331 and a second grating 332. The first grating 331 and the second grating 332 are each composed of a plurality of grating portions 330c arranged side by side along the Y-direction.

Here, in the third embodiment, as shown in FIG. 21, each of the first grating 331 and the second grating 332 is configured such that a plurality of grating portions 330c are arranged in a zigzag shape as viewed in the Z-direction, and thus, adjacent grating portions 330c overlap as viewed in the X-direction. More specifically, the plurality of grating portions 330c is arranged such that the grating portions 330c of columns C adjacent in the X-direction are offset from each other in the Y-direction in a state in which the columns C composed of the plurality of grating portions 330c arranged adjacent to each other along the Y-direction are arranged to form two columns along the X-direction.

Specifically, the second grating 332 includes a plurality of columns C1 and C2 of the grating portions 330c arranged adjacent to each other along the Y-direction. Column C1 is arranged on the X1 side of the second grating 332 and column C2 is arranged on the X2 side of the grating 332. Each of the plurality of grating portions 330c has a rectangular shape (polygonal shape) when viewed in the Z-direction. In the columns C1 and C2, the plurality of grating portions 330c each having a rectangular shape is arranged side by side along the Y-direction, so that a gap region 330e sandwiched by the grating regions 330d is formed between the plurality of grating portions 330c in the Y-direction. The plurality of grating portions 330c is arranged such that the sides 330f adjacent to each other in the Y-direction are substantially parallel in the X-direction when viewed in the Z-direction. That is, the gap region 330e formed between the plurality of grating portions 330c adjacent to each other in the Y-direction is substantially parallel to the X-direction when viewed in the Z-direction.

The columns C1 and C2 are arranged so as to be adjacent to each other along the X-direction when viewed in the Z-direction. The columns C1 and C2 are arranged so as to be adjacent to each other along the X-direction, so a gap region 330g is formed between the grating portions 330c adjacent to each other along the X-direction. The interval of the gap region 330g formed in the X-direction may be equal to or different from the interval of the gap region 330e formed in the Y-direction. In FIG. 21, an example is shown in which the interval of the gap region 330g is larger than that of the gap region 330e.

In the columns C1 and C2, the grating portions 330c are arranged so as to be shifted in the Y-direction so that the gap regions 330e formed in the columns C1 and C2 do not overlap when viewed in the X-direction. In the X-ray phase imaging apparatus 300, the columns C1 and C2 are arranged to be shifted in the Y-direction by half the length (½ pitches) of the grating portion 330c. As a result, (the grating regions 330d of) the adjacent grating portions 330c overlap with each other when viewed in the X-direction. Note that in FIG. 21, only the second grating 332 is shown as an example of the grating 330 composed of a plurality of grating portions 330c, but the configuration of the first grating 331 is the same.

With the above configuration, as shown in FIG. 22, in the X-ray phase imaging apparatus 300, in the same manner as in the X-ray phase imaging apparatus 100 according to the first embodiment, even when the subject P and the imaging system 10 are moved relative to each other in the X-direction, it is possible to make the subject P pass through the moiré fringe 40 (see FIG. 8) so as to include at least one period D4 (see FIG. 8) in the X-direction, not only when (each portion of) the subject P moves on the line 95 that does not include the gap region 330e but also when the subject P moves on the line 96 that includes the gap region 330e.

The other configurations of the X-ray phase imaging apparatus 300 according to the third embodiment are the same as those of the first embodiment.

Effects of Embodiment 3

In the third embodiment, the following effects can be obtained.

In the third embodiment, as described above, the plurality of grating portions 330c are arranged such that the columns C composed of the plurality of grating portions 330c arranged adjacent to each other along the third direction (Y-direction) are arranged in at least two columns along the first direction (X-direction), and the grating portions 330c of the columns C adjacent in the first direction are arranged in the third direction to each other, so that the plurality of grating portions 330c is arranged in a zigzag manner as viewed in the second direction (Z-direction), whereby the adjacent grating portions 330c overlap each other as viewed in the first direction.

As a result, it is possible to easily make the adjacent grating portions 330c overlap when viewed in the first direction by the plurality of grating portions 330c arranged in a zigzag shape when viewed in the second direction (Z-direction).

The other effects of the third embodiment are the same as those of the first embodiment.

Embodiment 4

Figure 23:
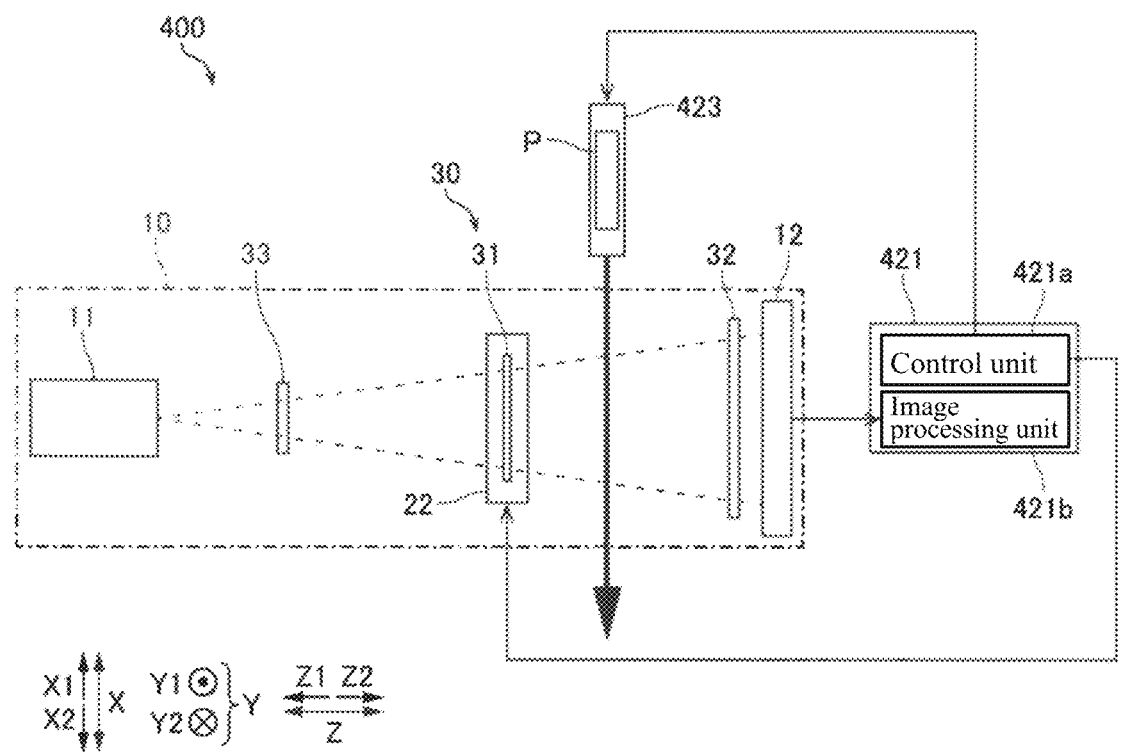
FIG. 23 is a diagram showing an entire configuration of an X-ray phase imaging apparatus according to a fourth embodiment.
Figure 24:
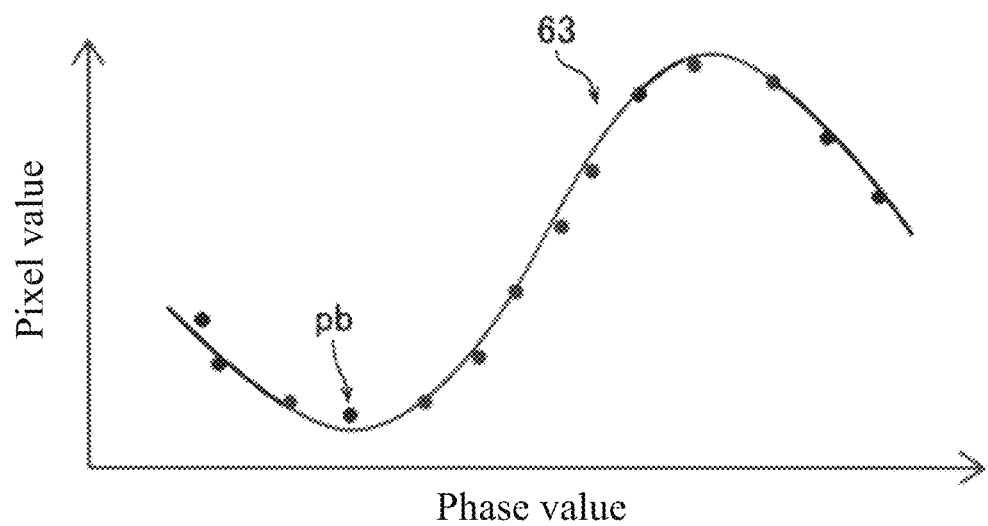
FIG. 24 is a diagram showing an intensity signal curve obtained by associating each phase value and each pixel value of each pixel of a plurality of images captured by the X-ray phase imaging apparatus according to the fourth embodiment in a one-to-one relation.
Figure 25:
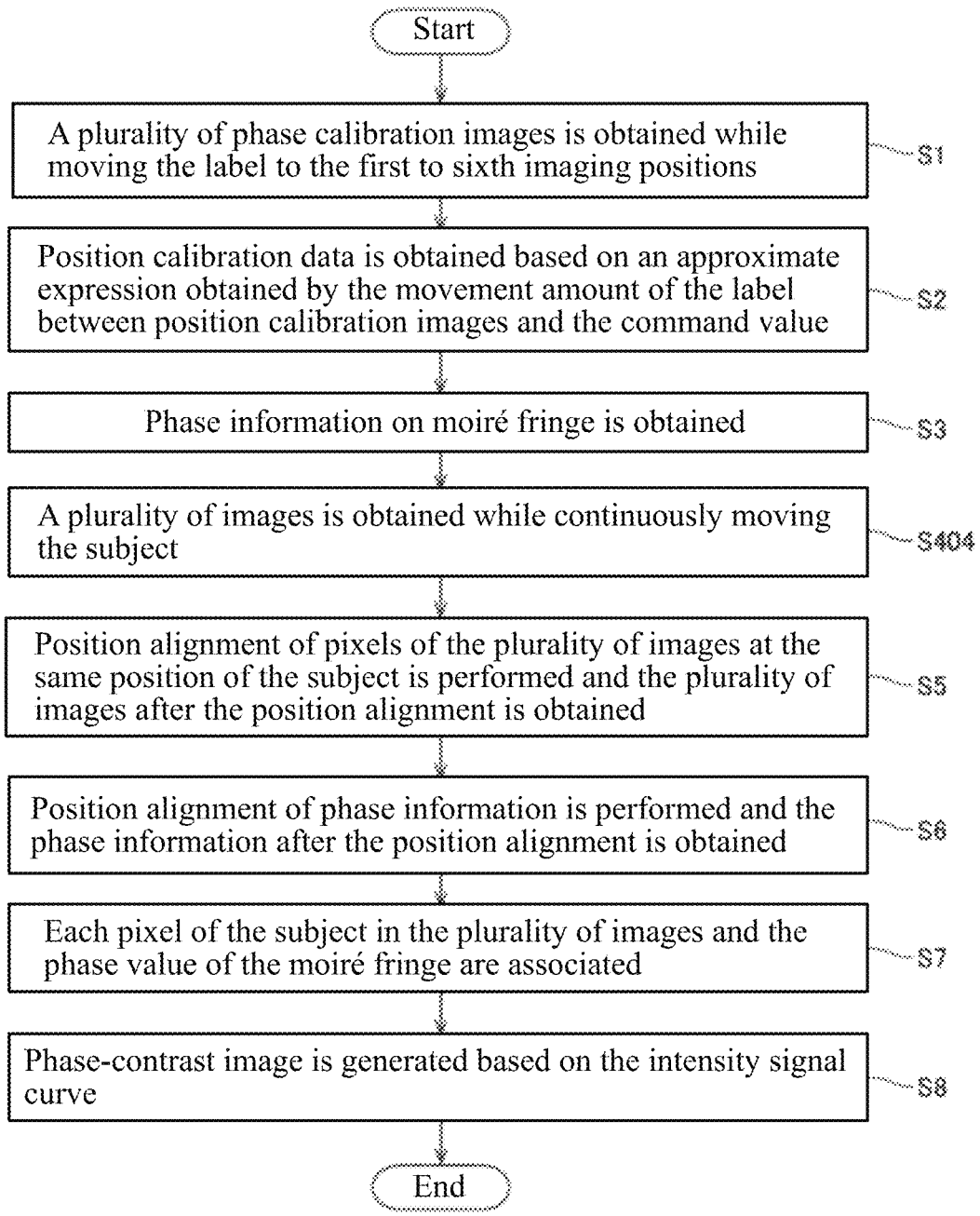
FIG. 25 is a flowchart for explaining a generation process of a phase-contrast image in the X-ray phase imaging apparatus according to the fourth embodiment.

With reference to FIG. 23 to FIG. 25, a fourth embodiment will be described. The fourth embodiment is configured to perform imaging while continuously moving the subject P, unlike the first embodiment configured to image the subject P at the first to sixth imaging positions. In the drawings, the same configuration portion as that of the first embodiment is denoted by the same reference symbol.

As shown in FIG. 23, the X-ray phase imaging apparatus 400 according to the fourth embodiment is provided with a processing unit 421 and a subject moving mechanism 423. The processing unit 421 includes a control unit 421a and an image processing unit 421b. Note that the subject moving mechanism 423 is an example of the "moving mechanism" recited in claims.

Here, in the fourth embodiment, the subject moving mechanism 423 is configured to continuously move the subject P along the direction (B-direction) of the grating pitch. In addition, the image processing unit 421b is configured to generate a phase-contrast image 51 (see FIG. 4) based on continuous images acquired by continuously performing imaging while continuously moving the subject P and the imaging system 10 relative to each other.

Specifically, under the control of the control unit 421a, the subject moving mechanism 423 is configured to be continuously movable in the X-direction in a state in which the subject P is placed on or held. The image processing unit 421b is configured to generate the phase-contrast image 51 (see FIG. 4) based on the acquired continuous subject images 52 (see FIG. 9) to acquire the subject images 52 as a moving image continuously captured at predetermined frame rates (time intervals).

As shown in FIG. 24, in the X-ray phase imaging apparatus 400, the subject images 52 (see FIG. 9) acquired as a moving image are aligned using position calibration data, and the phase information 41 is also aligned using position calibration data. Similarly to the first embodiment, the image processing unit 421b associates the pixel value of each pixel of the subject image 55 with the phase value of the moiré fringe 40 based on the pixel of each subject image 55 (see FIG. 13) after the alignment and the phase information 42 (see FIG. 14) after the alignment, and acquires the intensity signal curve 63 shown in FIG. 24. In the intensity signal curve 63, in the same manner as in the intensity signal curve 62 in the first embodiment, the horizontal axis represents phase values, and the vertical axis represents pixel values. In the same manner as in the first embodiment, the image processing unit 421b generates the phase-contrast image 51 (see FIG. 4) based on the intensity signal curve 63.

Phase-Contrast Image Generation Flow

Next, with reference to FIG. 25, a flow of generating the phase-contrast image 51 (see FIG. 4) by the X-ray phase imaging apparatus 400 according to the fourth embodiment will be described.

First, in Step S1 to Step S3, the same process as that of the first embodiment is performed.

Next, in Step S404, the control unit 421a acquires a plurality of subject images 52 while continuously moving the subject P by the subject moving mechanism 423.

Next, in Step S5 to Step S7, the same process as that of the first embodiment is performed. Then, in Step S8, the image processing unit 421b generates a phase-contrast image 51 and ends the process.

The other configurations of the X-ray phase imaging apparatus 400 according to the fourth embodiment are the same as those of the first embodiment.

Effects of Embodiment 4

In the fourth embodiment, the following effects can be obtained.

In the fourth embodiment, as described above, the subject moving mechanism 23 is configured to continuously move the subject P or the imaging system 10 along the direction (A-direction) in which the grating extends or along the direction (B-direction) of the grating pitch, and the image processing unit 21b is configured to generate the phase-contrast image 51 based on continuous images acquired by continuously performing imaging while continuously moving the subject P and the imaging system 10 relative to each other.

As a result, by performing imaging at several points (for example, six points) of the imaging position, the phase-contrast image 51 can be generated based on a larger number of images (subject images) 52 as compared with the case in which a plurality of images (subject images) 52 is acquired, so that the image quality of the phase-contrast image 51 can be improved.

The other effects of the fourth embodiment are the same as those of the first embodiment.

MODIFIED EXAMPLES

It should be noted that the embodiments disclosed herein are to be considered in all respects as illustrative and not restrictive. The scope of the present invention is indicated by claims rather than by the above description of the embodiments and includes all modifications (modified examples) within the meaning and range equivalent to the claims.

For example, in the first to fourth embodiments, an example is shown in which the X-ray phase imaging apparatus 100 (200, 300, 400) is configured to move the subject P and the imaging system 10 relatively by moving the subject P, but the present invention is not limited to this. In the present invention, in the same manner as in the X-ray phase imaging apparatus 500 according to the modified example of the first embodiment shown in FIG. 26, the X-ray phase imaging apparatus may be configured such that the subject P and the imaging system 10 are relatively moved by moving the imaging system 10.

Figure 26:
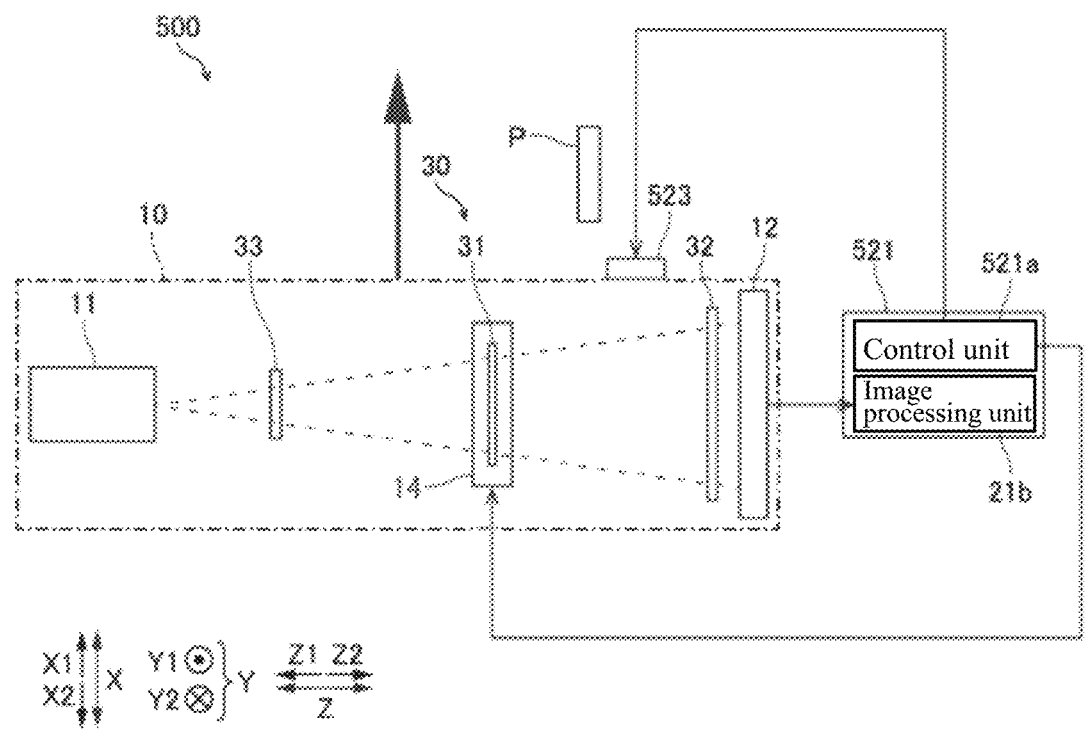
FIG. 26 is a diagram showing an entire configuration of an X-ray phase imaging apparatus according to a first modified example of the first embodiment.

As shown in FIG. 26, the X-ray phase imaging apparatus 500 is provided with a processing unit 521 and an imaging system moving mechanism 523. The processing unit 521 includes a control unit 521a. The imaging system moving mechanism 523 is configured to mount or hold the imaging system 10. The imaging system moving mechanism 523 is configured so as to be able to move the imaging system 10 in the X-direction by the control of the control unit 521a in a state in which the imaging system 10 is mounted or held. Note that the imaging system moving mechanism 523 is an example of the "moving mechanism" recited in claims.

In the first to fourth embodiments, an example is shown in which the first grating 31 (231, 331) and the second grating 32 (232, 332) are each composed of a plurality of grating portions 30c (230c, 330c) arranged side by side along the third direction (Y-direction), respectively, but the present invention is not limited to this. In the present invention, only one of the first grating and the second grating may be composed of a plurality of grating portions arranged side by side along the "third direction". In addition, the third grating may be composed of a plurality of grating portions arranged side by side along the "third direction".

In the first to fourth embodiments, an example is shown in which the plurality of grating portions 30c (230c, 330c) are arranged such that adjacent grating portions 30c (230c, 330c) overlap each other when viewed in the first direction so that at least one period D4 of the moiré fringe 40 is included in the first direction (X-direction) over the entire third direction (Y-direction), but the present invention is not limited thereto. In the present invention, a plurality of grating portions may be configured such that a part which is less than one period of a moiré fringe in the "first direction" in the "third direction". In this case, the subject needs to interpolate the information of the portion that has passed through the portion which is less than one period of the moiré fringe.

Further, in the first to fourth embodiments, an example is shown in which the sides 30f (330f) of the plurality of grating portions 30c (230c, 330c) adjacent in the third direction (Y-direction) extend linearly in a direction intersecting with the first direction (X-direction) when viewed in the second direction (Z-direction), but the present invention is not limited to this example. In this embodiment, like in the second modified example shown in FIG. 27, it may be configured such that the sides of the plurality of grating portions adjacent in the "third direction" extend in a curved manner in a direction intersecting with the "first direction" when viewed in the "second direction". It also may be configured such that adjacent sides of a plurality of grating portions adjacent in the "third direction" include a portion extending linearly in a direction intersecting with the "first direction" when viewed in the "second direction" and a portion extending curvilinearly.

Figure 27:
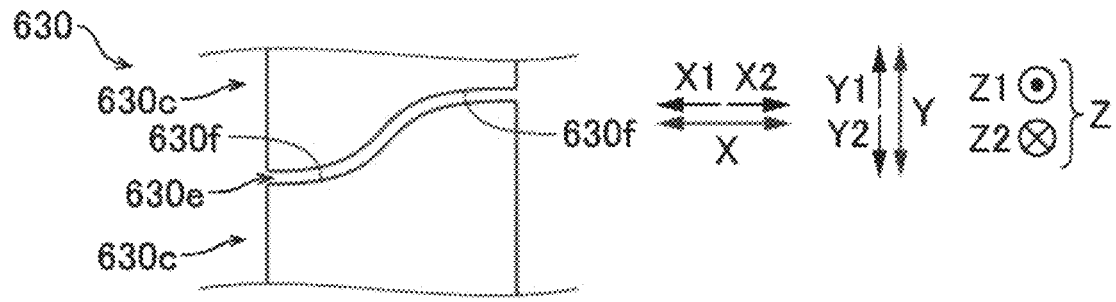
FIG. 27 is a diagram for explaining a plurality of grating portions of a grating of an X-ray phase imaging apparatus according to a second modified example of the first embodiment.

As shown in FIG. 27, the grating 630 is composed of a plurality of grating portions 630c arranged side by side along the Y-direction. A gap region 630e is formed between the plurality of grating portions 630c. The plurality of grating portions 630c extends in a curved shape such that the sides 630f of the plurality of grating portions 630c adjacent to each other in the Y-direction intersect with the X-direction when viewed in the Z-direction.

In the first to fourth embodiments described above, an example is shown in which the sides 30f (330f) of the plurality of grating portions 30c (230c, 330c) adjacent in the third direction (Y-direction) are configured to extend across the entire sides 30f (330f) as viewed in the second direction (Z-direction) in a direction intersecting with the first direction (X-direction), but the present invention is not limited thereto. In the present invention, as in the third modified example shown in FIG. 28, the sides adjacent of the plurality of grating portions in the "third direction" may extend in a direction intersecting with the "first direction" in only a portion of the sides when viewed in the "second direction".

Figure 28:
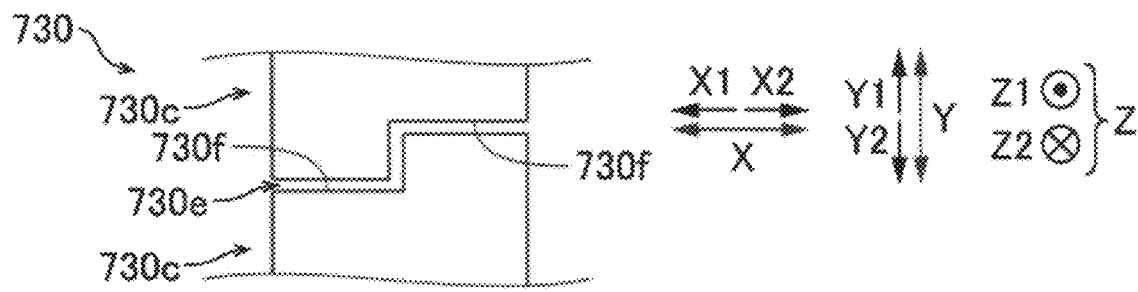
FIG. 28 is a diagram for explaining a plurality of grating portions of a grating of an X-ray phase imaging apparatus according to a third modified example of the first embodiment.

As shown in FIG. 28, the grating 730 is composed of a plurality of grating portions 730c arranged side by side along the Y-direction. A gap region 730e is formed between the plurality of grating portions 730c. The plurality of grating portions 730c includes a portion in which the sides 730f of the plurality of grating portions 730c adjacent to each other in the Y-direction extend linearly in a direction intersecting with the X-direction when viewed in the Z-direction and a portion in which the sides 730f extend linearly in a direction intersecting with the Y-direction.

In the first to fourth embodiments, an example is shown in which the plurality of grating portions 30c (230c, 330c) is arranged such that the sides 30f (330f) adjacent in the third direction (Y-direction) are substantially parallel to each other when viewed in the second direction (Z-direction). However, the present invention is not limited to this. In the present invention, the plurality of grating portions may be configured such that the sides adjacent in the "third direction" include portions that are not substantially parallel to each other when viewed in the "second direction".

In the second embodiment, although an example is shown in which the plurality of gratings 230 are arranged along an arc shape centered on the X-ray tube 11, the present invention is not limited to this example. In the present invention, the plurality of gratings may be arranged along a shape other than a shape along a circular arc centered on the X-ray tube as long as they are configured to have an arc shape convex toward the detection unit when viewed from the X-ray tube.

In the third embodiment, an example is shown in which the columns C composed of the plurality of grating portions 330c arranged adjacent to each other along the third direction (Y-direction) are arranged in two columns (columns C1 and C2) along the first direction (X-direction), and the columns C1 and C2 are arranged in the third direction (Y-direction) so as to be shifted by half (½) pitches) of the grating portion 330c, but the present invention is not limited to this. In this embodiment, as long as the gap regions formed in each of the two columns arranged along the "first direction" do not overlap when viewed in the "first direction", it may be configured such that the columns arranged along the "first direction" are arranged so as to be offset from each other by a length other than half of the grating portion in the "third direction".

In the third embodiment, an example is shown in which the columns C composed of the plurality of grating portions 330c arranged adjacent to each other along the third direction (Y-direction) are arranged in two columns along the first direction (X-direction), but the present invention is not limited to this. In the present invention, it may be configured such that a plurality of grating portions columns arranged adjacent to each other along the "third direction" is arranged in three or more columns along the "first direction".

In the first to fourth embodiments, an example is shown in which the X-ray phase imaging apparatus 100 (200, 300, 400) is configured to adjust the position of the first grating 31 (231, 331) in order to generate the moiré fringe 40 on the detection surface of the detection unit 12, but the present invention is not limited to this. In the present invention, the X-ray phase imaging apparatus may be configured to move the second grating or the third grating to generate a moiré fringe on the sensing surface of the detection unit.

Figure 29:
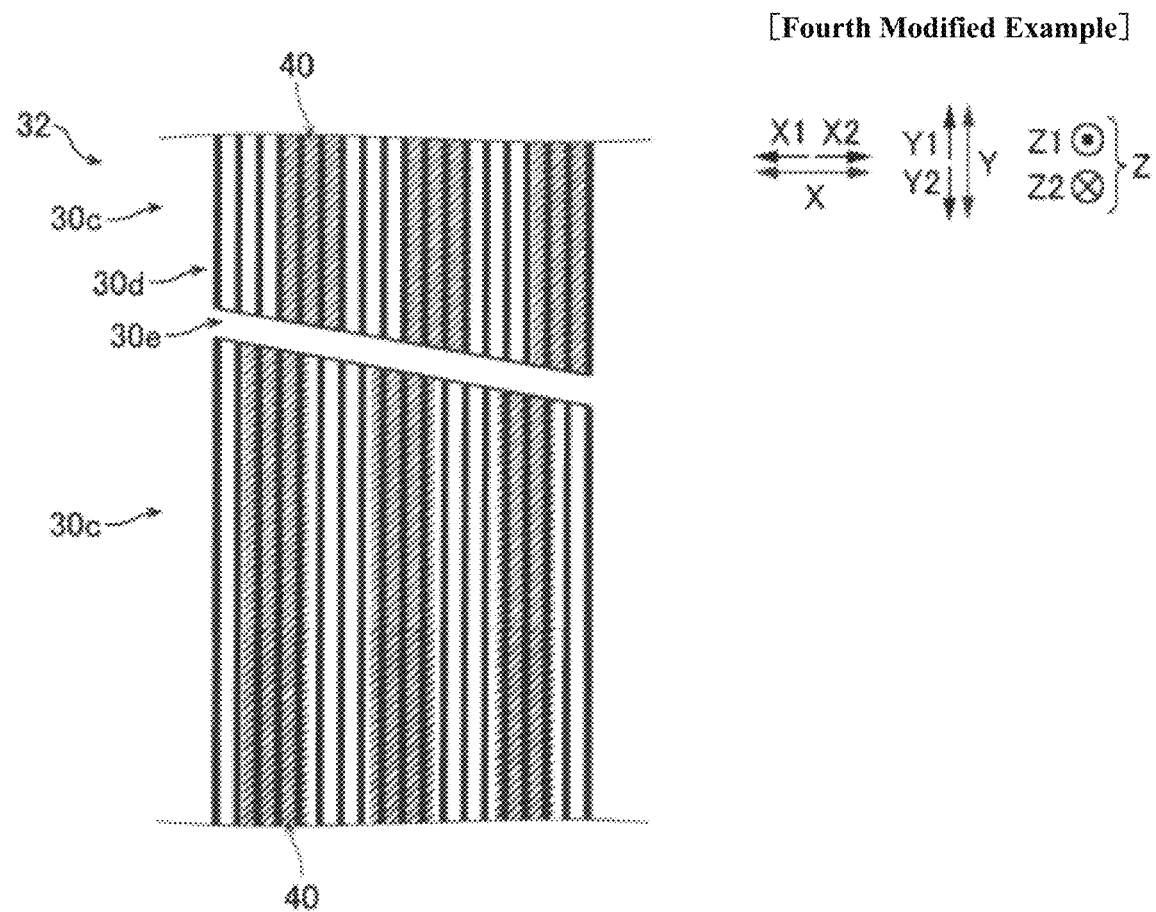
FIG. 29 is a diagram showing a moiré fringe generated at a position of a second grating in an X-ray phase imaging apparatus according to a fourth modified example of the first embodiment.

In the first to fourth embodiments, an example is shown in which the X-ray phase imaging apparatus 100 (200, 300, 400) is configured to generate the moiré fringes 40 substantially aligned in the first direction (X-direction) when viewed in the second direction (Z-direction) in any of the plurality of grating portions 30c (230c, 330c) arranged side by side along the third direction (Y-direction), but the present invention is not limited to this. In the present invention, like the fourth modification shown in FIG. 29, the X-ray phase imaging apparatus may be configured to generate moiré fringes shifted in the "first direction" when viewed in the "second direction" between a plurality of grating portions arranged side by side along the "third direction".

Figure 30:
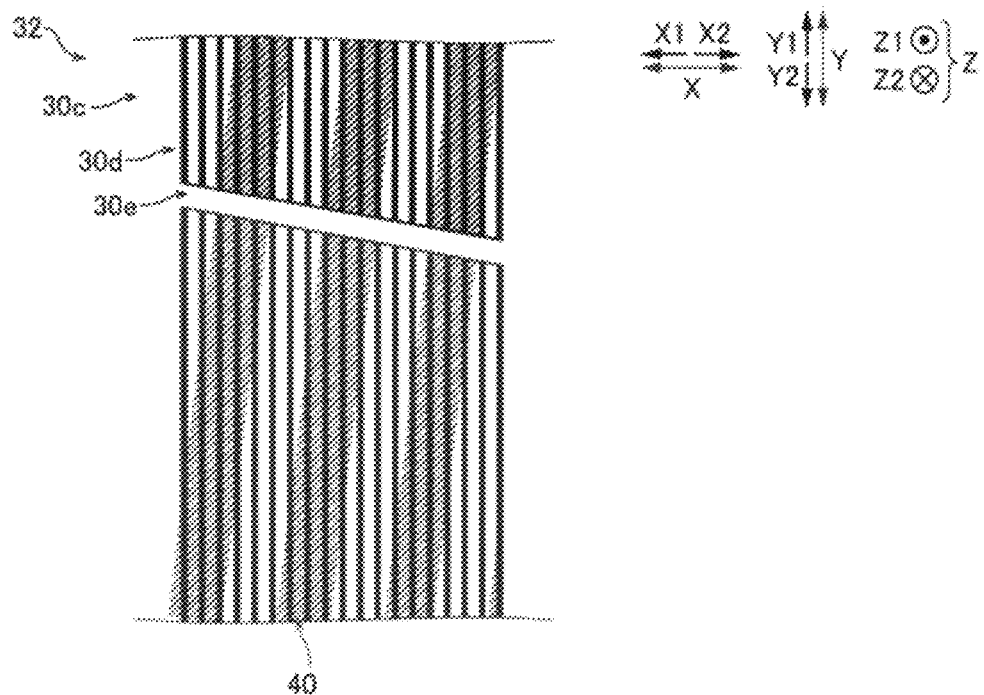
FIG. 30 is a diagram showing a moiré fringe generated at a position of a second grating in an X-ray phase imaging apparatus according to a fifth modified example of the first embodiment.

In the first to fourth embodiments, an example is shown in which the X-ray phase imaging apparatus 100 (200, 300, 400) is configured to perform imaging while relatively moving the subject P and the imaging system 10 in a state in which the moiré fringe 40 is generated in the first direction (X-direction) in which the subject P and the imaging system 10 are relatively moved, the present invention is not limited to this. In the present invention, like the fifth modified example shown in FIG. 30, the X-ray phase imaging apparatus may be configured to move the subject and the imaging system relative to each other in a state in which the moiré fringe is generated in a direction (crossing direction) different from the "first direction" in which the subject and the imaging system are moved relative to each other.

In the first to fourth embodiments, an example is shown in which the plurality of gratings 30 (230, 330) includes the third grating 33 (233) for enhancing the coherence of the X-rays emitted from the X-ray tube 11, but the present invention is not limited to this example. In the present invention, it may be configured such that the plurality of gratings does not include the third grating. In this case, it is desirable to use an X-ray tube which is high in coherence of X-rays emitted.

In the first to fourth embodiments, an example is shown in which the first grating 31 (231, 331) is used as a phase grating for generating a self-image by a Talbot effect, but the present invention is not limited to this example. In the present invention, since it is enough that the self-image is a striped pattern, an absorption grating may be used instead of a phase grating as the first grating. When an absorption grating is used, a region (non-interferometer) in which a fringe pattern is simply generated due to an optical condition such as a distance and a region (interferometer) in which a self-image due to a Talbot effect occurs are generated.

In the first to fourth embodiments described above, for convenience of explanation, the processes by the control unit 21a (421a) and the image processing unit 21b (421b) are described using a flowchart of a "flow-driven type", but the present invention is not limited to this. In the present invention, the processes of the control unit and the image processing unit may be performed in an "event-driven type" in which the processes are performed on an event-by-event basis. In this case, the operation may be performed in a complete event-driven type or in a combination of event-driven and flow-driven.

ASPECTS

It will be appreciated by those skilled in the art that the exemplary embodiments described above are illustrative of the following aspects.

Item 1
  An X-ray phase imaging apparatus comprising:
  an X-ray source;
  a detection unit configured to detect X-rays emitted from the X-ray source;
  a plurality of gratings arranged between the X-ray source and the detection unit to allow the X-rays emitted from the X-ray source to pass therethrough;
  a moving mechanism configured to move 1) a subject arranged between the X-ray source and the detection unit, 2) or an imaging system composed of the X-ray source, the detection unit and the plurality of gratings, along a direction in which the plurality of gratings extend or along a direction in which the plurality of gratings are arranged in a grating pitch; and
  an image processing unit configured to generate a phase-contrast image based on a plurality of images acquired based on signals detected by the detection unit with the subject and the imaging system being relatively moved with respect to each other,
  wherein at least one of the plurality of gratings is composed of a plurality of grating portions arranged along a third direction perpendicular to a first direction in which the subject or the imaging system is moved by the moving mechanism and a second direction in which the X-ray source, the detection unit, and the plurality of gratings are arranged, and
  wherein the plurality of grating portions are arranged so that adjacent grating portions overlap when viewed in the first direction.

Item 2
  The X-ray phase imaging apparatus as recited in the aforementioned Item 1,
  wherein the image processing unit is configured to generate the phase-contrast image based on a pixel value of each pixel in the plurality of images and phase information on a moiré fringe generated in the plurality of images, and
  wherein the plurality of grating portions are arranged such that adjacent grating portions overlap when viewed in the first direction so that at least one period of the moiré fringe is included in the first direction throughout the third direction.

Item 3
  The X-ray phase imaging apparatus as recited in the aforementioned Item 1 or 2, wherein a gap region sandwiched by grating regions is formed between the plurality of grating portions arranged along the third direction, and wherein the plurality of grating portions are arranged such that adjacent grating portions overlap when viewed in the first direction so that at least the grating region is included in the first direction throughout the third direction.

Item 4
  The X-ray phase imaging apparatus as recited in any one of the aforementioned Items 1 to 3,
  wherein each of the plurality of grating portions have a polygonal shape when viewed in the second direction, and wherein sides of the plurality of grating portions arranged adjacent to each other along the third direction arranged in the third direction are arranged to include a portion extending in a direction intersecting with the first direction when viewed in the second direction, so that the grating portions adjacent to each other overlap when viewed in the first direction.

Item 5
  The X-ray phase imaging apparatus as recited in the aforementioned Item 4, wherein the plurality of grating portions are arranged such that sides of the plurality of grating portions adjacent to each other in the third direction arranged adjacent to each other in the third direction extend in a direction intersecting with the first direction over an entirety of the sides when viewed in the second direction.

Item 6
  The X-ray phase imaging apparatus as recited in the aforementioned Item 4 or 5, wherein the plurality of grating portions are arranged such that the sides of the plurality of grating portions adjacent in the third direction are substantially parallel to each other when viewed in the second direction Item 7
  The X-ray phase imaging apparatus as recited in any one of the aforementioned Items 4 to 6,
  wherein the moving mechanism is configured to move the subject or the imaging system along a direction along which the gratings of the plurality of gratings extend, and
  wherein at least one of the gratings composed of the plurality of grating portions are arranged side by side along an arc having a convex arc shape toward a detection unit side when viewed in the first direction.

Item 8
  The X-ray phase imaging apparatus as recited in any one of the aforementioned Items 1 to 3,
  wherein in the plurality of grating portions, in a state in which columns composed of the plurality of grating portions arranged adjacent to each other in the third direction are arranged in at least two columns along the third direction, the grating portions of adjacent columns in the first direction are arranged offset in the third direction, so that the plurality of grating portions are arranged in a zigzag manner as viewed in the second direction, whereby the grating portions adjacent to each other overlap as viewed in the first direction.

Item 9
  The X-ray phase imaging apparatus as recited in any one of the aforementioned Items 1 to 8,
  wherein the moving mechanism is configured to continuously move the subject or the imaging system in 1) a direction along which the gratings extend or 2) along a direction of the grating pitch, and
  wherein the image processing unit is configured to generate the phase-contrast image based on continuous images acquired by continuously performing imaging with the subject and the imaging system being relatively moved with respect to each other.

The invention claimed is:

1. An X-ray phase imaging apparatus comprising:
an X-ray source;
a detection unit configured to detect X-rays emitted from the X-ray source;
a plurality of gratings arranged between the X-ray source and the detection unit to allow the X-rays emitted from the X-ray source to pass therethrough, each of the plurality of gratings comprising a plurality of slits extending in a slit extension direction and arranged in a slit pitch direction;
a moving mechanism configured to move 1) a subject arranged between the X-ray source and the detection unit, or 2) an imaging system composed of the X-ray source, the detection unit and the plurality of gratings, along the slit extension direction or along the slit pitch direction; and
an image processing unit configured to generate a phase-contrast image based on a plurality of images acquired based on signals detected by the detection unit with the subject and the imaging system being relatively moved with respect to each other,
wherein at least one of the plurality of gratings is composed of a plurality of grating portions arranged along a third direction perpendicular to a first direction in which the subject or the imaging system is moved by the moving mechanism and a second direction in which the X-ray source, the detection unit, and the plurality of gratings are arranged,
wherein the plurality of grating portions are arranged so that adjacent grating portions overlap when viewed in the first direction,
wherein a gap region sandwiched by grating regions is formed between the plurality of grating portions arranged along the third direction, and
wherein the plurality of grating portions are arranged such that adjacent grating portions overlap when viewed in the first direction so that at least the grating region is included in the first direction throughout the third direction.

2. The X-ray phase imaging apparatus as recited in claim 1,
wherein the image processing unit is configured to generate the phase-contrast image based on a pixel value of each pixel in the plurality of images and phase information on a moiré fringe generated in the plurality of images, and
wherein the plurality of grating portions are arranged such that adjacent grating portions overlap when viewed in the first direction so that at least one period of the moiré fringe is included in the first direction throughout the third direction.

3. The X-ray phase imaging apparatus as recited in claim 1,
wherein each of the plurality of grating portions form a polygonal shape when viewed in the second direction, and
wherein a pair of adjacent grating portions of the plurality of grating portions are arranged adjacent to each other along the third direction, the pair of adjacent grating portions having opposing sides that face each other, each opposing side including a portion extending in a direction intersecting with the first direction when viewed in the second direction, so that the pair of adjacent grating portions overlap when viewed in the first direction.

4. The X-ray phase imaging apparatus as recited in claim 3,
wherein each of the plurality of grating portions comprise a pair of opposite sides that extend in the third direction,
wherein each of the opposing sides of the pair of adjacent grating portions extend between and connect to the corresponding pair of opposite sides of the corresponding one of the pair of adjacent grating portions, and
wherein the entirety of each of the opposing sides of the pair of adjacent grating portions extend in the direction intersecting with the first direction between the corresponding pair of opposite sides of the corresponding one of the pair of adjacent grating portions when viewed in the second direction.

5. The X-ray phase imaging apparatus as recited in claim 3,
wherein the plurality of grating portions are arranged such that the opposing sides of the pair of grating portions that intersect with the first direction are substantially parallel to each other when viewed in the second direction.

6. The X-ray phase imaging apparatus as recited in claim 3,
wherein the moving mechanism is configured to move the subject or the imaging system along the slit extension direction, and
wherein the plurality of grating portions are arranged side by side along an arc having a convex arc shape toward a detection unit side when viewed in the first direction.

7. The X-ray phase imaging apparatus as recited in claim 1,
wherein the moving mechanism is configured to continuously move the subject or the imaging system in 1) the direction along which the gratings extend or 2) along the direction of the grating pitch, and
wherein the image processing unit is configured to generate the phase-contrast image based on continuous images acquired by continuously performing imaging with the subject and the imaging system being relatively moved with respect to each other.

8. The X-ray phase imaging apparatus as recited in claim 1, wherein each of the plurality of grating portions form parallelogram shape when viewed in the second direction.

9. The X-ray phase imaging apparatus as recited in claim 1, wherein the gap region is larger than a grating pitch of the grating portions.

10. The X-ray phase imaging apparatus as recited in claim 1, wherein, with respect to a view in the second direction, the gap region has a substantially constant width.

11. The X-ray phase imaging apparatus as recited in claim 1, wherein, with respect to the projection view in the second direction, the slit extension direction is parallel to the first sides and the second sides and extends in the third direction.

12. The X-ray phase imaging apparatus as recited in claim 1, wherein the plurality of grating portions of the at least one of the plurality of gratings is arranged in a single column arranged along the third direction.

13. An X-ray phase imaging apparatus comprising:
an X-ray source;
a detection unit configured to detect X-rays emitted from the X-ray source;
a plurality of gratings arranged between the X-ray source and the detection unit to allow the X-rays emitted from the X-ray source to pass therethrough, each of the plurality of gratings comprising a plurality of slits extending in a slit extension direction and arranged in a slit pitch direction;

a moving mechanism configured to move 1) a subject arranged between the X-ray source and the detection unit, or 2) an imaging system composed of the X-ray source, the detection unit and the plurality of gratings, along the slit extension direction or along the slit pitch direction; and an image processing unit configured to generate a phase-contrast image based on a plurality of images acquired based on signals detected by the detection unit with the subject and the imaging system being relatively moved with respect to each other, wherein at least one of the plurality of gratings is composed of a plurality of grating portions arranged along a third direction perpendicular to a first direction in which the subject or the imaging system is moved by the moving mechanism and a second direction in which the X-ray source, the detection unit, and the plurality of gratings are arranged, wherein the plurality of grating portions are arranged so that adjacent grating portions overlap when viewed in the first direction, wherein, with respect to a projection view in the second direction, the plurality of grating portions each have a first side and second side opposite to and parallel with the first side, the first sides of the grating portions extending in the third direction and being colinear with each other and the second sides extending in the third direction and being colinear with each other, and wherein, with respect to the projection view in the second direction, for each pair of adjacent grating portions, a first side of one of the pair of adjacent grating portions and a second side of the other of the pair of adjacent grating portions overlap each other with respect to the first direction.

* * * * *